United States Patent [19]

McIlroy et al.

[11] Patent Number: 5,583,758
[45] Date of Patent: Dec. 10, 1996

[54] HEALTH CARE MANAGEMENT SYSTEM FOR MANAGING MEDICAL TREATMENTS AND COMPARING USER-PROPOSED AND RECOMMENDED RESOURCES REQUIRED FOR TREATMENT

[75] Inventors: Gary T. McIlroy, Edina; Julie E. Kees, Eagan; Jacquelyn A. Kalscheuer, Bloomington, all of Minn.

[73] Assignee: Health Risk Management, Inc., Minneapolis, Minn.

[21] Appl. No.: 475,523

[22] Filed: Jun. 7, 1995

Related U.S. Application Data

[63] Continuation of Ser. No. 449,288, May 24, 1995, which is a continuation of Ser. No. 901,642, Jun. 22, 1992.

[51] Int. Cl.$^6$ ................................................. G06F 17/60
[52] U.S. Cl. .................................... 395/202; 395/209
[58] Field of Search .............................. 364/401, 402, 364/403, 408

[56] References Cited

U.S. PATENT DOCUMENTS

| | | | |
|---|---|---|---|
| 1,988,634 | 1/1935 | Stonecypher | 35/12 |
| 3,186,111 | 1/1965 | Lawlor | 35/17 |
| 3,566,370 | 2/1971 | Worthington, Jr. et al. | 340/172.5 |
| 3,794,982 | 2/1974 | McCormick et al. | 340/172.5 |
| 3,810,102 | 5/1974 | Parks, III et al. | 340/172.5 |
| 3,934,226 | 1/1976 | Stone et al. | 340/172.5 |
| 3,970,996 | 7/1976 | Yasaka et al. | 340/172.5 |
| 4,290,114 | 9/1981 | Sinay | 364/900 |
| 4,315,309 | 2/1982 | Coli | 364/200 |
| 4,360,345 | 11/1982 | Hon | 434/262 |
| 4,464,122 | 8/1984 | Fuller et al. | 434/262 |
| 4,489,387 | 12/1984 | Lamb et al. | 364/514 |
| 4,583,524 | 4/1986 | Hutchins | 128/1 R |
| 4,667,292 | 5/1987 | Mohlenbrock et al. | 364/406 |
| 4,731,725 | 3/1988 | Suto et al. | 364/415 |
| 4,733,354 | 3/1988 | Potter et al. | 364/415 |
| 4,737,912 | 4/1988 | Ichikawa | 364/413 |
| 4,839,822 | 6/1989 | Dormond et al. | 364/513 |
| 4,858,126 | 8/1989 | Croce, Jr. | 364/413.02 |
| 4,899,758 | 2/1990 | Finkelstein et al. | 128/672 |
| 4,945,476 | 7/1990 | Bodick et al. | 364/413.02 |
| 5,018,067 | 5/1991 | Mohlenbrock et al. | 364/413.02 |
| 5,025,374 | 6/1991 | Roizen et al. | 364/413.02 |
| 5,029,081 | 7/1991 | Kagawa | 364/413.01 |
| 5,084,819 | 1/1992 | Dewey et al. | 364/419 |
| 5,088,037 | 2/1992 | Battaglia | 364/413.01 |

OTHER PUBLICATIONS

Wilson, Anne S., et al., "Designing a Guideline-Based Utilization Management Program," *Benefits Quarterly*, Forth Quarter, pp. 42–47, (1991).

Greenes, Robert A., "Computer-Aided Diagnostic Strategy Selection," *The Radiologic Clinics of North America*, vol. 24, No. 1, pp. 105–120, (Mar. 1986).

Affidavit of Julie Kees (5 pages), with attached exhibits (A–M).

A Quick Introduction to MRP, B. McSpaden, System User, vol. 5, No. 4 pp. 16–17, Jul. 1984.

Naval Submarine Medical Research Laboratory, NSMRL Report 1141, 23 Jun. 1989, Karen Fisherkeller & Robert Beaudrg.

Structuring Coherent Explanation: The use of Diagnostic Strategie in an Expert Critiquing System, Pradeep Mutalik, Paul Fisher, H. A. Swett, P. L. Miller.

Primary Examiner—Gail O. Hayes
Assistant Examiner—Hayward A. Verdun
Attorney, Agent, or Firm—Schwegman, Lundberg, Woessner & Kluth, P.A.

[57] ABSTRACT

A health care management system for use by hospitals, physicians, insurance companies, health maintenance organizations, and others in the health care field includes a processing unit and health condition guidelines. A user inputs information related to the health condition of an individual and guideline treatment options are identified. The user also inputs actual or proposed and final recommendation treatments for the same individual. The resulting comparative information can be used to modify the actual or proposed treatment, or provide explanatory information as to reasons for the difference between the final recommendation treatment and guideline treatment options. Also, the comparative information can be used by a reviewer for evaluation or utilization purposes.

5 Claims, 35 Drawing Sheets

Fig.2a

| MED CAT NUM | MEDICAL CATEGORY DESCRIPTION | GL NUM | GL EXT | GUIDE LINE DESCRIPTION |
|---|---|---|---|---|
| 52 | BLOOD/INFECTIOUS DISEASE | 90 | | BLOOD/INFECTIOUS DISEASE; EST, SURGICAL |
| | | 91 | | BLOOD/INFECTIOUS DISEASE; EXT, MEDICAL |
| 53 | CARDIOVASCULAR/RESPIRATORY | 01 | | ANGINA, STABLE; REQUESTING ANGIOGRAM |
| | | 02 | | MI, ACUTE |
| | | 03 | X | MI, ACUTE; EXTENSION |
| | | 05 | | PNEUMONIA, ADULT |
| | | 08 | | ASTHMA, BRONCHIAL |
| | | 09 | | PULMONARY EMBOLI |
| | | | X | PULMONARY EMBOLI; EXTENSION |
| | | | | CHEST PAIN |
| | | | | ANGINA, UNSTABLE |
| | | | | PRE-INFARCTION SYNDROME |
| | | 10 | X | CHEST PAIN; EXTENSION |
| | | | | CORONARY ARTERY DISEASE (CAD) |
| | | | | ARTERIOSCLEROTIC HEART DISEASE (ASHD) |
| | | 13 | X | CORONARY ARTERY DISEASE; EXTENSION |
| | | | | CHF |
| | | 15 | | CONGESTIVE HEART FAILURE |
| | | 20 | | ARRHYTHMIA |
| | | 22 | | VARICOSE VEINS |
| | | | | ARTERIAL OCCLUSIVE DISEASE, PERIPHERAL |
| | | | | FEMORAL-POPLITEAL OCCLUSION |
| | | | | FEMORAL-TIBIAL OCCLUSION |
| | | | | AORTIC-ILIAC OCCLUSION |

Fig. 2b

| | | | |
|---|---|---|---|
| 54 | CENTRAL NERVOUS SYSTEM | 23 | DEEP VEIN THROMBOSIS |
| | | 33 | THROMBOPHLEBITIS |
| | | | THROMBOPHLEBITIS; EXTENSION —15 |
| | x | 90 | PNEUMONIA, PEDIATRIC |
| | | 91 | CARDIOVASCULAR/RESPIRATORY; EXT, SURG. |
| | | 01 | CARDIOVASCULAR/RESPIRATORY; EXT, MEDICAL |
| | | 02 | NEURO DEFICIT, MOTOR OR SENSORY |
| | | | TIA |
| | | 09 | TRANSIENT ISCHEMIC ATTACK |
| | | 90 | MULTIPLE SCLEROSIS |
| | | 91 | CENTRAL NERVOUS SYSTEM; EXT, SURGICAL |
| | | | CENTRAL NERVOUS SYSTEM; EXT, MEDICAL |
| 55 | OTOLARYNGOLOGY/OPHTHALMOLOGY | 01 | SEPTUM DEVIATION, NASAL |
| | | 02 | NASAL OBSTRUCTION |
| | x | | SINUSITIS, ACUTE |
| | | | SINUSITIS, ACUTE; EXTENSION |
| | | 10 | TONSILLITIS, ACUTE |
| | | 11 | TONSILLITIS, CHRONIC |
| | | | TONSILLITIS, RECURRENT |
| | | 13 | OTITIS MEDIA, ACUTE |
| | | 14 | OTITIS MEDIA, CHRONIC |
| | | 16 | TONSILLAR HYPERTROPHY |
| | | 54 | SINUSITIS, CHRONIC; MAXILLARY/ETHMOID |
| | | 55 | SINUSITIS, CHRONIC; FRONTAL |
| | | 57 | NASAL/SINUS POLYPS |
| | | 58 | SINUSITIS, SPHENOID |

Fig. 3

| GUIDE LINE (16) | DX CODE (17) |
|---|---|
| 53(05) | 49311 |
|  | 49321 |
|  | 49390 |
|  | 49391 |
| 53(08) | 4151 |
| 53(08X) | 4151 |
| 53(09) | 4111 |
|  | 4139 |
|  | 4140 |
|  | 4149 |
|  | 4280 |
|  | 78650 |
| 53(09X) | 4111 |
|  | 4139 |
|  | 4140 |
|  | 4149 |
|  | 4280 |
|  | 78650 |
| 53(10) | 4111 |
|  | 4139 |
|  | 4140 |
|  | 4149 |
| 53(10X) | 4111 |
|  | 4139 |
|  | 4140 |
|  | 4149 |
| 53(13) | 40291 |
|  | 4280 |
| 53(15) |  |
| 53(20) | 4540 |
|  | 4541 |
|  | 4549 |
|  | 45981 |
| 53(22) | 25070 |
|  | 25071 |
|  | 4402 |
|  | 4423 |
|  | 44389 |
|  | 4439 |
|  | 44422 |
|  | 44481 |
|  | 4471 |
| 53(23) | 4439 |
|  | 44422 |
|  | 44489 |
|  | 4449 |
|  | 45119 |

Fig. 4

| GUIDE LINE | QUES NUMBER/DESCRIPTION | FRM PASS | FRM | FAIL |
|---|---|---|---|---|
| 53(22) | 01B PAIN AT REST IN THE LEG, MAY INCLUDE NIGHT PAIN | 02 — 23a | | |
| | 01C GANGRENE OF FOOT | 02 | | |
| | 01D NON-HEALING ULCERATION OF FOOT | 02 | | |
| | 01E NONE OF THE ABOVE | PR | | |
| | 02 PATIENT HAS HAD ARTERIOGRAM | 03 | 4A | 4B |
| | 03 HIGH GRADE STENOSIS >75% OR COMPLETE OCCLUSION | 04 | PR | 2A |
| | 04 LENGTH OF LESION < 5 CM | 4C 4D 4E 4F | 4F | |
| 53(23) | 01 DEEP VEIN THROMBOSIS DIAGNOSED ON DOPPLER/VENOGRAM | 03 | 02 | |
| | 02M SUPERFICIAL THROMBOPHLEBITIS DIAGNOSED BY EXAM AND ONE OF THE FOLLOWING: | | | |
| | 02A PAIN | 05 | | |
| | 02B REDNESS | 05 | | |
| | 02C SWELLING | 05 | | |
| | 02D NONE OF THE ABOVE | PR | | |
| | 03 IS THERE PROXIMAL EMBOLIZATION? | OT | 04 | |
| | 04M ANTICOAGULATION THERAPY CONTRAINDICATED DUE TO: | | | |
| | 04A SENSITIVITY TO HEPARIN | 4A — 23b | | |
| | 04B GI OR INTRACEREBRAL BLEED | 4A | | |
| | 04C PATIENT HAS CA OR ESPECIALLY METASTATIC CA | 4A | | |
| | 04D OTHER CONTRAINDICATION | 4A | | |
| | 04E NO CONTRAINDICATION | 2A 2B | | |
| | 05 PATIENT HAS PROGRESSIVE SYMPTOMS DESPITE APPROPRIATE OP MANAGEMENT (INCLUDES ANTIBIOTICS, REST, HOT PACKS AND/OR NSAID'S) | 2C | | |
| 53(23X) | 01 MEDICAL MANAGEMENT FAILED | 4A | | |
| 53(33) | 01M DIAGNOSED ON IMAGING AND ONE OF THE FOLLOWING: | | | |

Fig.5

| GUIDE LINE | QUES NUMBER/DESCRIPTION | FRM | PASS | FAIL |
|---|---|---|---|---|
| 55(91) | 01M ONE OF THE FOLLOWING: | | | |
| | 01A PERSISTENT NAUSEA AND/OR VOMITING AND/OR UNABLE TO TOLERATE LIQUID DIET X24 HOURS | | 2A | |
| | 01B ABNORMAL LABS, ONE OR MORE OF THE FOLLOWING:<br>-ELEVATED WBC < =12,000 MM<br>-ELEVATED TEMPERATURE > =100 F (37.7 C), ORAL<br>-POSITIVE BLOOD CULTURE | | 2B | |
| | 01C CONTINUED INFECTIOUS SYMPTOMS (SWELLING, REDNESS, PAIN) AND OUTPATIENT TREATMENT CONTRAINDICATED | | 2C | |
| | 01D MEDICATION COURSE CHANGED DUE TO CULTURE RESULTS | | 2D | |
| | 01E ACUTE CLOSED ANGLE GLAUCOMA, INTRAOCCULAR PRESSURE ELEVATED | | 2E | |
| | 01F NONE OF THE ABOVE | | PR | |
| 56(01) | 01M DOES THE PATIENT HAVE ANY COMBINATION OF THESE: | | | |
| | 01A RLQ TENDERNESS | | 02 | |
| | 01B ABDOMINAL PAIN | | 02 | |
| | 01C REBOUND TENDERNESS | | 02 | |
| | 01D NAUSEA/VOMITING | | 02 | |
| | 01E PERIUMBILICAL PAIN | | 02 | |
| | 01F LEUKOCYTOSIS | | 02 | |
| | 01G NONE OF THE ABOVE | | 03 | |
| | 02 PRESENCE OF AN ABSCESS OR PERITONITIS ASSOCIATED WITH THE APPENDICITIS | | 4A | 4B |
| | 03 HISTORY OF PREVIOUSLY CONSERVATIVELY TREATED APPENDICITIS | | 4C 4D | PR |
| 56(01X) | 01 LAPAROSCOPIC APPENDECTOMY FAILED, DID OPEN PROCEDURE | | 4A | 56(90) |
| 56(02) | 01 DX MADE BY IMAGING, I.E.:<br>ULTRASOUND<br>CHOLECYSTOGRAM<br>DISIDA | | 02 | PR |

Fig.6

| GUIDE LINE | QUES NUMBER/DESCRIPTION | FRM PASS | | FAIL |
|---|---|---|---|---|
| 53(03) | 04A AGE >65 | 2B | 2C | |
| | 04B IMMUNOSUPPRESSED | 2B | 2C | |
| | 04C COMORBID ILLNESS (DIABETES, CHF, COPD, ASTHMA, RENAL FAILURE TB, MALIGNANCY | 2B | 2C | |
| | 04D HIGH RISK PNEUMONIA ETIOLOGY SUSPECTED OR CONFIRMED BY CULTURE STAPHYLOCOCCAL, GRAM NEGATIVE ROD, ASPIRATION) | 2B | 2C | |
| | 04E LUNG ABSCESS, EMPYEMA, CAVITARY LESIONS WITH OR WITHOUT RELATED INFECTION | 2B | 2C | |
| | 04F HIV AND/OR AIDS PNEUMOCYSTITIS** | 2B | 2C | |
| | 04G NONE OF THE ABOVE | 02P | 2A | 2C |
| | | 03A | 2A | 2C |
| | | 03B | 2A | 2C |
| | | 03C | 2A | 2C |
| | | 03D | 2A | 2C |
| | | 03E | 2A | 2C |
| | | 03F | PR | |
| 53(05) | 01 DIAGNOSED BY HISTORY/KNOWN ASTHMATIC | 02 | | OT PR |
| | 02M EMERGENCY TREATMENT INITIATED WITH CONTINUED PRESENCE OF ONE OF THE FOLLOWING: | | | |
| | 02A SPIROMETRY RESULTS OF: FEB1 < 60% OF PREDICTED OR PEAK FLOW < 40% OF PREDICTED | 2A | 2B | |
| | 02B BLOOD GAS RESULTS OF: PCO2 >40mmHg OR PO2 < 60mmHg OR O2 SATURATION < 90% | 2A | 2B | |
| | 02C PRESENTING SIGNS OR SYMPTOMS OF: USE OF ACCESSORY MUSCLES OR ABNORMAL VITAL SIGNS (RESPIRATORY RATE >26/MINUTE, PLUSE >102/MINUTE) | 2A | 2B | |
| | 02D SEVERE DYSPNEA EVEN AFTER TREATMENT WITH INHALED MEDS | 2A | 2B | |
| | 02E NONE OF THE ABOVE | PR | | |
| 53(08) | 01M DIAGNOSTIC RESULTS OF ONE OF THE FOLLOWING: | | | |
| | 01A HIGHLY PROBABLE LUNG SCAN | 03 | | |
| | 01B POSITIVE PULMONARY ANGIOGRAM | 03 | | |

Fig.7

| GUIDE LINE 25 | REC NUM 26 | CODE 33 | 27 | SETTING 28 | A/S 29 | LOS 30 | PREOP 31 | FLAG 32 |
|---|---|---|---|---|---|---|---|---|
| 53(23) | OT | A0001 | OTHER DIAGNOSIS | OP | N | 0 | 0 | |
| | PR | A0002 | PHYSICIAN REVIEW | OP | N | 0 | 0 | |
| | 2A | C0005 | IV HEPARIN AND COUMADIN (COUMADIN MUST BE INITIATED BY AT LEAST DAY 2 OF HEPARINIZATION) | 1P | N | 7 | 0 | |
| | 2B | C0007 | STREPTOKINASE OR UROKINASE FOR 3 DAYS FOLLOWED BY 6 DAYS HEPARIN WITH COUMADIN INITIATED BY DAY 2 OF HEPARINIZATION | 1P | N | 9 | 0 | |
| | 2C | C0008 | BED REST, WITH OR WITHOUT ANTIBIOTICS, WITH OR WITHOUT ANTICOAGULANTS, WITH OR WITHOUT NSAID'S | 1P | N | 2 | 0 | |
| | 2D | C0019 | ANTIBIOTICS, REST, HOT PACKS AND/OR NSAID'S | 1P | N | 2 | 0 | |
| | 4A | 34421 | EMBOLECTOMY OR THROMBECTOMY, VENA CAVA, ILIAC, FEMOROPOPLITEAL VEIN BY LEG INCISION | 1P | N | 7 | 0 | |

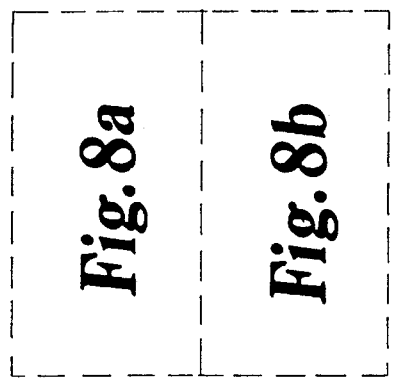

| 34 | 35 SETTING | 36 LOS | 37 PREOP LOS | 38 A/S | 39 FLAG | 40 LINE NUM | 41 CPT VERBAGE |
|---|---|---|---|---|---|---|---|
| C0001 | 1P | 4 | 0 | N |   | 02 | WITHOUT OXYGEN |
| C0001C | 1P | 7 | 0 | N | * | 01 | (*IF AIDS REFER CCM) |
| C0002 | 1P | 7 | 0 | N | CCM | 01 | PARENTERAL ANTIBIOTIC WITH VENTILATOR |
| C0003 | 1P | 4 | 0 | N |   | 01 | INHALED BETA AGONISTS WITH SYSTEMIC |
|  |  |  |  |  |  | 02 | STERIODS (IV OR PO) OF >40 MG PREDNISONE |
|  |  |  |  |  |  | 03 | OR EQUIVALENT PER DAY WITH OR WITHOUT |
|  |  |  |  |  |  | 04 | THEOPHYLLINES WITH OR WITHOUT |
|  |  |  |  |  |  | 05 | ANTICHOLINERGICS |
| C0003C | 1P | 4 | 0 | N | CCM | 01 | ON VENTILATOR |
| C0004 | 1P | 6 | 0 | N | CCM | 01 | PARENTERAL MEDICATIONS WITH OR WITHOUT |
|  |  |  |  |  |  | 02 | OXYGEN |
| C0005 | 1P | 7 | 0 | N |   | 01 | IV HEPARIN AND COUMADIN (COUMADIN MUST |
|  |  |  |  |  |  | 02 | BE INITIATED BY AT LEAST DAY 2 OF |
|  |  |  |  |  |  | 03 | HEPARINIZATION) |
| C0006 | OP | 0 | 0 | N |   | 01 | ANTIPLATELET/ANTICOAGULANT MEDICAL |
|  |  |  |  |  |  | 02 | MANAGEMENT |
| C0007 | 1P | 9 | 0 | N |   | 01 | STREPTOKINASE OR UROKINASE FOR 3 DAYS |
|  |  |  |  |  |  | 02 | FOLLOWED BY 6 DAYS HEPARIN WITH |
|  |  |  |  |  |  | 03 | COUMADIN INITIATED BY DAY 2 OF |
|  |  |  |  |  |  | 04 | HEPARINIZATION |
| C0008 | 1P | 7 | 0 | N |   | 01 | BED REST, WITH OR WITHOUT ANTIBIOTICS, |
|  |  |  |  |  |  | 02 | WITH OR WITHOUT ANTICOAGULANTS, WITH OR |
|  |  |  |  |  |  | 03 | WITHOUT NSAID'S |
| C0009 | OP | 0 | 0 | N |   | 01 | STABILIZE CLINICAL CONDITION, IF |
|  |  |  |  |  |  | 02 | POSSIBLE, PRIOR TO FURTHER CARDIAC |

Fig. 8b

| Code | Type | | | | Description |
|---|---|---|---|---|---|
| C0010 | OP | 0 | 0 | | 03 EVALUATION |
| C0011 | 1P | 7 | 0 | N | 01 MEDICAL MANAGEMENT |
| C0011C | 1P | 10 | 0 | N | 01 CCU WITH TELEMETRY |
| C0012 | 1P | 7 | 0 | N | 01 WITH CC |
| C0013 | 1P | 3 | 0 | N | 01 STREPTOKINASE OR TPA |
| C0014 | OP | 0 | 0 | N | 01 CCU WITH TELEMETRY AND MEDICATION |
| C0015 | 1P | 3 | 0 | N | 02 REGULATION |
| C0016 | 1P | 2 | 0 | N | 01 ANTIBIOTICS, ORAL |
| C0016C | 1P | 3 | 0 | N | 01 TELEMETRY WITH CARDIAC MEDICATION |
| C0017 | OP | 0 | 0 | N | 01 TELEMETRY, SERIAL IKGS AND ENZYMES |
| C0018 | OP | 0 | 0 | N | 01 WITH ANGINAL EQUIVALENT |
| | | | | | 01 EXERCISE THALLIUM OR TECHNETIUM SCAN |
| | | | | | 01 ADENOSINE OR PERSANTINE SCAN IF AVAIL-ABLE |
| C0019 | OP | 0 | 0 | N | 02 ANTIBIOTICS, REST, HOT PACKS |
| | | | | | 01 AND/OR NSAID'S |
| C0020 | OP | 0 | 0 | N | 02 EXERCISE STRESS TEST |
| C0021 | 1P | 3 | 0 | N | 01 NG SUCTION |
| C0022 | 1P | 3 | 0 | N | 01 TPN |
| C0023 | 1P | 2 | 0 | N | 01 OBSERVATION |
| | | | | | 02 WITH OR WITHOUT IV |
| | | | | | 03 ANTIBIOTICS, WITH OR WITHOUT IV FLUIDS |
| C0024 | 1P | 2 | 0 | N | 04 WITH OR WITHOUT INVESTIGATIONAL STUDIES |
| | | | | | 01 IV ANTIBIOTICS, WITH OR WITHOUT DAILY |
| | | | | | 02 DRESSING CHANGES |
| C0025 | 1P | 2 | 0 | N CCM | 01 IM ANALGESICS >=q4h OR IV ANALGESICS |

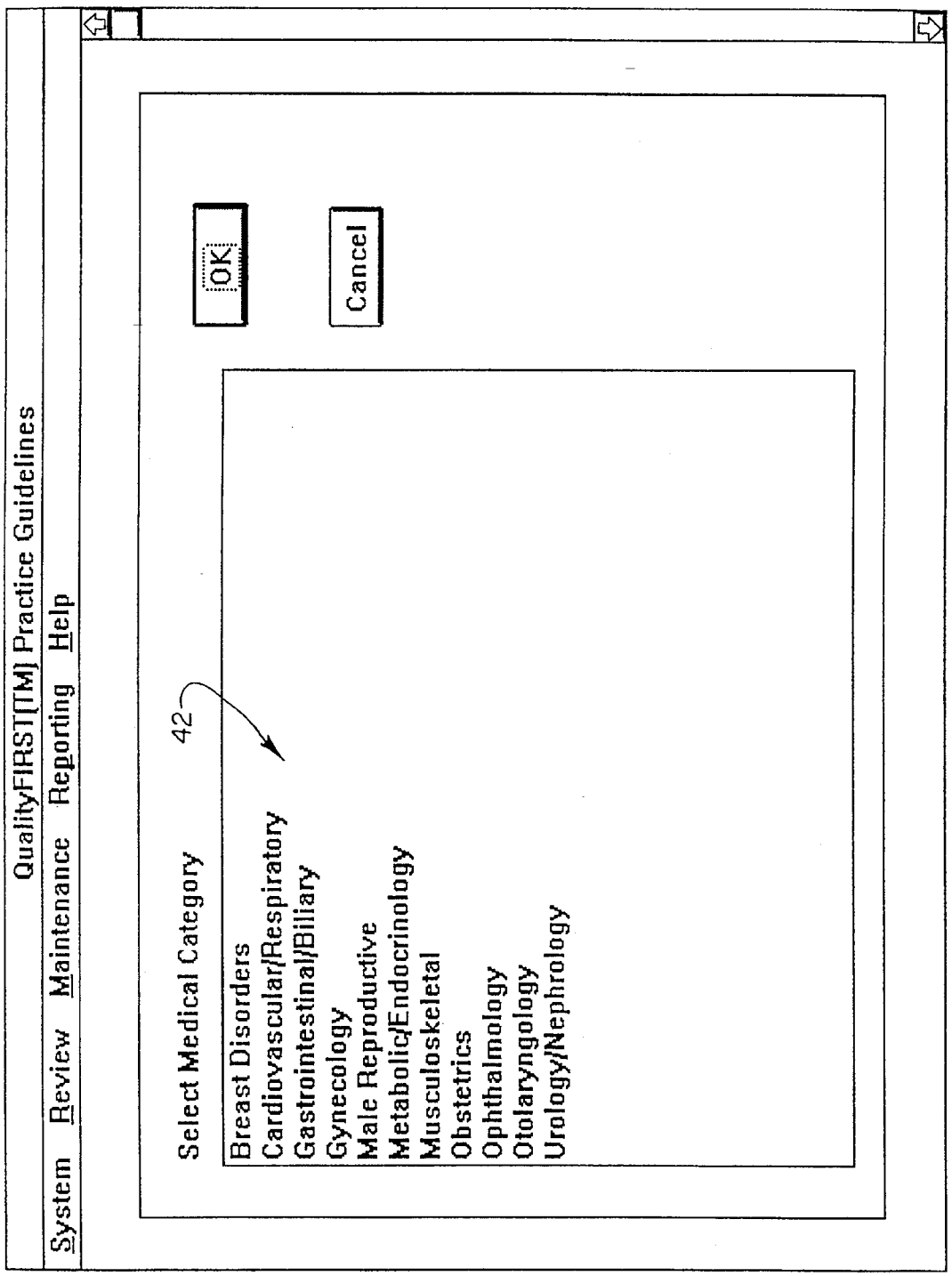

Fig.14

Cardiovascular/Respiratory: Thrombophlebitis

View  Conclude  Undo  Enter  Help

Initial Review, Case not yet entered

1  Deep vein thrombosis diagnosed on doppler/venogram     [Pass] [Fail]     P/F

2  Superficial thrombophlebitis diagnosed by exam and one of the following:     No Selection

[a] pain

[b] redness

[c] swelling

[d] none of the above

3  Is there proximal embolization?     P/F

4  Anticoagulation therapy contraindicated due to:     No Selection

[a] sensitivity to heparin

[b] GI or intracerebral bleed

[c] patient has CA or especially metastatic CA

Fig.15

Cardiovascu[lar]

View  Conclude  Undo  Enter  He[lp]

Initial R[eview]

Treatment
Recommended= 2A,2B

2A] IV heparin and coumadin [couma[din]
be initiated by at least day 2 of
heparinization]

2B] Streptokinase or urokinase for 3
followed by 6 days heparin with
coumadin initiated by day 2 of
heparinizaton 2C] Bed rest, with or without antibioti[cs]
with or without anticoagulants, w[ith]
without NSAID'S 4A] Embolectomy or thrombectomy,
iliac, femoropopliteal vein by leg
incision OT] Other Diagnosis
PR] Physician review
PO]

53
54

---

Specialist Review

Case ID#: N/A

Review #: N/A          Specialist Review #: N/A

ID:  [JKEES]

Type:
○ Clinical Review
● Physician Review
○ IME
○ Appeal

[OK]

[Cancel]

[Print]

Reason:  ☒ Appropriate Treatment Plan
         ☐ Partial Procedure
         ☐ Setting
         ☐ LOS
         ☐ Preop Days
         ☐ Assistant Surgeon
         ☐ Diagnosis Confirmation

Fig.16

Cardiovascular/Respiratory: Thrombophlebitis

View  Conclude  Undo  Enter  Help

Initial Review, Case not yet entered

Treatment
Recommended = 2A,2B — 58

| | 59 [#] | Setting 60 | LOS 61 [#d] | Preop 63 [#d] | A/S 62 | Flag 64 |
|---|---|---|---|---|---|---|
| 2A] IV heparin and coumadin [coumadin must be initiated by at least day 2 of heparinization] | — | IP | 07 | — | N | |
| 2B] Streptokinase or urokinase for 3 days followed by 6 days heparin with coumadin initiated by day 2 of heparinizaton | | IP | 09 | | N | |
| 2C] Bed rest, with or without antibiotics, with or without anticoagulants, with or without NSAID'S | | IP | 02 | | N | |
| 2D] Antibiotics, rest hot packs and/or NSAID's | | IP | 02 | | N | |

57

| | Proposed | | | Final Recommendation | | | Reason | Care Changed |
|---|---|---|---|---|---|---|---|---|
| Treatment — 69 | 2A | N | | 2A | N | | | |
| Setting — 65 | IP ⇨ | IP | | IP | IP | | | ⇨ ⇨ |
| LOS — 66 | 9 | 7 | | 9 | 7 | | | ⇨ ⇨ |
| Preop Days — 67 | 0 | 0 | | 0 | 0 | | C | ⇨ ⇨ |
| (Assistant Surgeon 68) | ⇨ | N | | ⇨ | N | | | ⇨ ⇨ |

Dx Confirmation?

[OK]  Cancel  Close  Print

Fig. 17

Cardiovascular/Respir
View  Conclude  Undo  Enter  He[lp]    Initial R

Treatment
Recommended= 4A,4B

4A] Angiogram, coronary with left he[art] catheterization
[may allow up to 1 day if unable outpatient]
4B] Angiogram, coronary with left he[art] catheterization
with cc, patient has diabetes, ren[al] failure or CHF
4C] Exercise stress test
4D] Exercise Thallium or Technetium
4E] Adenosine or persantine scan if able
PR] Physician review
PO]

---

Specialist Review

Case ID#: N/A —70
Review #: N/A —71    Specialist Review #: N/A—72

ID: [ JKALS ]—73

Type:
○ Clinical Review—74
⦿ Physician Review—75
○ IME—76
○ Appeal—77

[OK]
[Cancel]
[Print]

Reason: ☒ Appropriate Treatment Plan—78
☐ Partial Procedure—79
☐ Setting—80
☐ LOS—81
☐ Preop Days—82
☐ Assistant Surgeon—83
☐ Diagnosis Confirmation—84

DATE  DAILY PRODUCTIVITY REPORT  PAGE 1
OPERATION MANAGER

| MEDICAL CATEGORY | OPEN REVIEWS | # TO SPECIALIST REVIEW (204) | OPEN <=30 DAYS (206) | OPEN >30 DAYS (205) |
|---|---|---|---|---|
| CARDIOVASCULAR/RESPIRATORY | | | | |
| 202~INITIAL | 24 | 4 | 22 | 2 |
| 203~EXTENSION | 6 | 1 | 6 | 0 |
| TOTAL | 30 | 5 | 28 | 2 |
| GYNECOLOGY | | | | |
| INITIAL | 10 | 2 | 10 | 0 |
| EXTENSION | 2 | 0 | 2 | 0 |
| TOTAL | 12 | 2 | 12 | 0 |
| 201 TOTAL INITIAL | 34 | 6 | 32 | 2 |
| EXTENSION | 8 | 1 | 8 | 0 |
| TOTAL | 42 | 7 | 40 | 2 |

(200 MEDICAL CATEGORY)

FIG. 19

DATE DAILY PRODUCTIVITY REPORT PAGE 1
SUPERVISOR

MEDICAL CATEGORY: CARDIOVASCULAR/RESPIRATORY

| CARE MANAGER | REVIEW TYPE | OPEN REVIEWS | # TO SPECIALIST REVIEW (211) | OPEN <=30 DAYS (213) | OPEN >30 DAYS (212) |
|---|---|---|---|---|---|
| ABCDE | 208 ~ INITIAL | 24 | 4 | 22 | 2 |
|  | 209 ~ EXTENSION | 6 | 1 | 6 | 0 |
|  | 207 ~ TOTAL | 30 | 5 | 28 | 2 |
| DEFGH | INITIAL | 10 | 2 | 10 | 0 |
|  | EXTENSION | 2 | 0 | 2 | 0 |
|  | TOTAL | 12 | 2 | 12 | 0 |
| TOTAL | INITIAL | 34 | 6 | 32 | 2 |
|  | EXTENSION | 8 | 1 | 8 | 0 |
|  | TOTAL | 42 | 7 | 40 | 2 |

FIG. 20

DATE　　　　　　　　　DAILY PRODUCTIVITY REPORT　　　　　　　　　　　　PAGE 1
　　　　　　　　　　　　　　　CARE MANAGER

CARE MANAGER: ABCDE {NAME} ⌒214

| CASE ID ⌒215 | REVIEW DATE ⌒216 | INIT/ EXT ⌒217 | SPEC TYPE ⌒218 | REFERRAL REASON ⌒219 | GUIDELINE ⌒220 |
|---|---|---|---|---|---|
| 05801112223 | 05/01/92 | I | PR | TPLAN | ANGINA, STABLE |
| 05801112223 | 05/05/92 | E | | | ANGINA, STABLE |
| 01112222333 | 05/10/92 | I | PR | SET | DEGENERATIVE JOINT DISEASE |
| 01233332229 | 05/01/92 | I | | LOS | DEGENERATIVE JOINT DISEASE |

FIG. 21

DATE                    DAILY PRODUCTIVITY REPORT                                               PAGE 1
                          SPECIALIST REVIEWER

SPECIALIST REVIEWER: XYZAB ⌐221

| CASE ID ⌐222 | REVIEW DATE ⌐223 | INIT/ EXT ⌐224 | SPEC TYPE ⌐225 | REFERRAL REASON ⌐226 | GUIDELINE ⌐227 |
|---|---|---|---|---|---|
| 0508111112223 | 05/01/92 | I | PR | TPLAN | ANGINA, STABLE |
| 0580111112223 | 05/05/92 | E | PR | LOS | ANGINA, STABLE |
| 0111222223333 | 05/10/92 | I | PR | SET | DEGENERATIVE JOINT DISEASE |
|  |  |  |  | LOS |  |
| 0123333332229 | 05/01/92 | I | PR | TPLAN | DEGENERATIVE JOINT DISEASE |

FIG. 22

DATE                      DAILY PRODUCTIVITY REPORT                PAGE 1
SPECIALIST REVIEWER PRODUCTIVITY

MEDICAL CATEGORY: CARDIOVASCULAR/RESPIRATORY
SPECIALIST TYPE: PR PHYSICIAN REFERRAL

| CASE ID (228) | REVIEW DATE (229) | INIT/EXT (230) | SPEC ID (231) | REFERRAL REASON (232) | GUIDELINE (233) |
|---|---|---|---|---|---|
| 0580111122223 | 05/01/92 | I | XYZAB | TPLAN | ANGINA, STABLE |
| 0580111122223 | 05/05/92 | E | XXXXY | LOS | ANGINA, STABLE |
| 0111222223333 | 05/10/92 | I | XYZAB | SET | THROMBOPHLEBITIS |
|  |  |  |  | LOS |  |
| 0123333322229 | 05/01/92 | I | XYZAB | TPLAN | ARTERIAL OCCLUSIVE DISEASE |

FIG. 23

| DATE | SPECIALIST REVIEW WORK SHEET | PAGE 1 |
|---|---|---|

SPECIALIST REVIEWER: XYZAB ~ 234        RETURN TO: _____

CARE MANAGER:  ABCDE   235        BY (DATE): _____
      CASE ID:  000005100001  REVIEW #: 2
  CLINICIAN ID:  A00100 ~ 236
  REVIEW DATE:  6/05/92
     DIAGNOSIS:  CALCULUS, URETERAL

PROPOSED TREATMENT: ~ 237        SETTING  LOS  PREOP
  A/S
4A) CYSTOSCOPY WITH RETROGRADE STONE    IP    *02    0    N
    MANIPULATION

238
GUIDELINE RECOMMENDED TREATMENT:    SETTING  LOS  PREOP
  A/S
4A) CYSTOSCOPY WITH RETROGRADE STONE    IP    01    0    N
    MANIPULATION
4B) URETEROSCOPY/URETEROPYELOSCOPY    IP    01    0    N
4C) CYSTOSCOPY WITH JJ STENT PLACEMENT   OP               N

QUESTIONS PASSED: 239
    DIAGNOSED BY IMAGING AND ONE OF THE FOLLOWING:
        FLANK PAIN - SEVERE REQUIRING IM PAIN MEDS

ONE OF THE FOLLOWING:
        - HIGH GRADE OBSTRUCTION
        - SEVERE INTRACTABLE PAIN
        - STONE TOO LARGE TO PASS

QUESTIONS FAILED: 240

REASON FOR SPECIALIST REVIEW:
    APPROPRIATE TREATMENT PLAN
    LENGTH OF STAY

NOTE TEXT INFORMATION: 241
    CYSTO URETHROSCOPY STONE EXTRACTION INSERTION STENT
    ATTEMPTED WO SUCCESS PERC NEPH DONE DUE TO URINE
    EXTRAVASATION TEMP PO ORAL ABS TEACH PERC NEPH CARE MONITOR

SPECIALIST REVIEW WORK SHEET PAGE 2

DATE _____

SPECIALIST REVIEWER: XYZAB

CASE ID:    000005100001   REVIEW #: 2
    CLINICIAN ID:  A00100
    REVIEW DATE:  6/05/92
    DIAGNOSIS:  CALCULUS, URETERAL

⌠242
FINAL RECOMMENDATION (DOCUMENT
CHANGES ONLY)

|  | REASON CODE ⌠243 | CARE CHANGED? ⌠243a |
|---|---|---|
| *TREATMENT: _____ | _____ | Y N U |
| SETTING: IP OP OF _____ | _____ | Y N U |
| *LOS: ____ DAYS _____ | _____ | Y N U |
| PREOP: ____ DAYS _____ | _____ | Y N U |
| A/S: Y N S _____ | _____ | Y N U |
| *DX CONFIRM Y N _____ | _____ | Y N U |

| CASE VOLUME: | 1,245 ~244 |
|---|---|
| REVIEW VOLUME: | 1,999 ~245 |
| # PHYSICIANS: | 42 ~246 |
| # GUIDELINES: | 70 ~247 |

FIG. 25

| MEDICAL CATEGORY: CARDIOVASCULAR/RESPIRATORY | | | |
|---|---|---|---|
| GUIDELINE | CASES (248) | % OF CASES (249) | % OF TOTAL CASES (250) |
| CORONARY ARTERY DISEASE | 50 | 35.0 | 10.0 |
| ANGINA, STABLE | 20 | 10.0 | 4.0 |
| ANGINA, UNSTABLE | 20 | 10.0 | 4.0 |
| ASTHMA | 10 | 5.0 | 2.0 |
| PNEUMONIA | 14 | 7.0 | 2.8 |
| ARTERIAL OCCLUSIVE DISEASE | 5 | 2.5 | 1.0 |
| • | • | • | |
| • | • | • | |
| • | • | • | |
| SUBTOTAL | 200 | 100.0 | 40.0 |
| TOTAL | 500 | 100.0 | 100.0 |

FIG. 26

MEDICAL CATEGORY: CARDIOVASCULAR/RESPIRATORY

| GUIDELINE | CASES (251) | PROPOSED TREATMENT (252) | CASES (253) | PROPOSED AVG LOS (254) | AVG LOS RECOMMENDED (255) |
|---|---|---|---|---|---|
| CORONARY ARTERY DISEASE | 50 | PTCA | 47 | 3 | 3 |
| | | CABG, 3 GRAFTS | 3 | 9 | 8 |
| ANGINA, UNSTABLE | 20 | TELEMETRY | 3 | 2 | 2 |
| | | TELEMETRY/ PACEMAKER | 2 | 3 | 3 |
| | | TELEMETRY/ ANGIOGRAM | 10 | 4 | 3 |
| | | ANGIOGRAM W/CC* | 2 | 1 | 1 |
| | | ANGIOGRAM WO/CC* | 3 | 1 | 0 |
| ARTERIAL OCCLUSIVE DISEASE | 5 | ARTERIOGRAM | 2 | 2 | 1 |
| | | BYPASS | 3 | 8 | 7 |

*COMORBIDITY

FIG. 27

GUIDELINE: (5310) CORONARY ARTERY DISEASE ~256a

CASES: 50 ~256

| 257 TREATMENT 258 | | 259 | 260 | 261 % TO | VARIANCE | | 265 -CARE CHANGED- | |
|---|---|---|---|---|---|---|---|---|
| PROPOSED | FINAL | CASES | % | SPEC REV | VOLUME | CODE | % | KNOWN |
| PTCA | PTCA | 45 | 90 | 11 | 5 | A(4) | | |
| CABG/ 3 GRAFT | CABG/ 3 GRAFT | 3 | 6 | 33 | | K(1) | | |
| | | | | | 1 ~262 | F(1) 263 264 | | |
| PROPOSED = FINAL: | | 48 | 96 | | | | | |
| PTCA | MEDICAL MANAGEMENT | 2 | 4 | 100 | | | 50 | 100 |
| PROPOSED ≠ FINAL: | | 2 | 4 | | | | | |

FIG. 28

GUIDELINE: (5310) CORONARY ARTERY DISEASE ~266  PAGE 1

| | 268 TREATMENT 272 | | | 277 | 278 | 279 | 281 CARE CHANGED |
|---|---|---|---|---|---|---|---|
| 267 PROPOSED | FINAL | CASES | % | % TO SPEC REV | EXT RATE | GL VARIANCE VOLUME CODE* | % KNOWN |
| PTCA 273 | PTCA 274 | 45 275 | 90.0 276 | | | | |
| 269 --SETTING-- | | | | | | | |
| IP | IP | 45 | 100.0 | | | | |
| PROPOSED = FINAL: | | 45 | 100.0 | | | | |
| --PREOP (0)-- | | | | | | | |
| 270  0 | 0 | 43 | 95.0 | 0.0 | | | |
| 1 | 1 | 1 | 2.5 | 100.0 | | 1 | |
| PROPOSED = FINAL: | | 44 | 97.5 | | | | |
| 1 | 0 | 2.5 | 100.0 | | | | |
| PROPOSED ≠ FINAL: | | 1 | 2.5 | | | A(1) 280 280a | |
| --LOS-- | | | | | | | |
| 271  3 | 3 | 35 | 77.8 | | | | |
| 4 | 4 | 5 | 11.1 | 20.0 | 20.0 | 5 | |
| PROPOSED = FINAL: | | 40 | 88.9 | | | | |
| 4 | 3 | 5 | 11.1 | 10.0 | | | |
| PROPOSED ≠ FINAL: | | 5 | 11.1 | | | H(4) K(1) | 80.0  50 |

* KEY  A - COMORBIDITY
      H = SOCIAL SITUATION
      K = AGE

FIG. 29

| GUIDELINE 282 | % REVIEW IMPACT PROPOSED TREATMENT 283 | % REVIEW IMPACT PROPOSED RESOURCES 284 | REVIEWS IMPACTED BOTH RESOURCES AND TREATMENT 285 | % CASES IMPACTED 286 | # CASES 287 |
|---|---|---|---|---|---|
| CORONARY ARTERY DISEASE | 4 | 13 | 1 | 14 | 50 |
| ANGINA, UNSTABLE | 1 | 25 | 0 | 30 | 20 |
| ARTERIAL OCCLUSIVE DISEASE | 0 | 40 | 0 | 40 | 5 |

FIG. 30

HEALTH CARE MANAGEMENT SYSTEM FOR MANAGING MEDICAL TREATMENTS AND COMPARING USER-PROPOSED AND RECOMMENDED RESOURCES REQUIRED FOR TREATMENT

This patent is a continuation of Ser. No. 08/449,288 filed May 24, 1995 entitled "Health Care Management System," which is a file-wrapper continuation of Ser. No. 07/901,642 filed Jun. 22, 1992 entitled "Health Care Management System." This patent is related to Ser. No. 08/478,273 filed Jun. 7, 1995 "Health Care Management System" which is continuation of Ser. No. 08/449,288 filed May 24, 1995 entitled "Health Care Management System," which is a file-wrapper continuation of Ser. No. 07/901,642 filed Jun. 22, 1992 entitled "Health Care Management System," and to Ser. No. 08/475,207 filed Jun. 7, 1995 entitled "Data Structure for Health Care Management System" which is a continuation of Ser. No. 08/449,288 filed May 24, 1995 entitled "Health Care Management System," which is a file-wrapper continuation of Ser. No. 07/901,642 filed Jun. 22, 1992 entitled "Health Care Management System."

BACKGROUND OF THE INVENTION

The present invention pertains to the field of data processing systems for health care management. More specifically, the present invention pertains to a health care management data processing system for use by hospitals, physicians, insurance companies, health maintenance organizations (HMO's), and others in the health care field to serve as a diagnostic, evaluation, and utilization tool for health care provided to individuals. The system is implemented in computer hardware and software.

Due to the increasing complexity and cost of providing health care, there is an ever increasing emphasis on managing the health care process. The process extends from an individual presenting a health concern to a health care provider and continues through diagnosis, therapeutic selection, resource selection, treatment, and follow-up. This process could be extended further to include proactively identifying or preventing health concerns and planning for anticipated resource needs at one end of the process, and daily nursing management and disability management at the other end of the process.

Previous efforts to manage health care included manual-historical systems where individual files recording actual treatment provided were manually reviewed to collect statistics on general categories of care or to review the appropriateness of in a given case. Such methods are labor-intensive and inefficient. Efforts have been made to standardize data collection forms, descriptions of conditions, descriptions of treatment, and treatments in order to more efficiently collect and evaluate health care data. Other efforts have been made to automate the analysis of historical health care data for persons with particular health care conditions. These efforts focus mainly on collecting financial data and serve accounting and administrative functions.

At least one known automated prior art health care management system addresses therapeutic selection by starting with a selected treatment and, based on patient information provided by the user, evaluating whether or not that treatment is appropriate. See "Guideline-based Utilization Management Program", *Benefits Quarterly* (4th Quarter 1991). Such systems do not develop a treatment based on various data describing an individual's health condition; the user must first select a predefined treatment. Also, these systems do not have the flexibility to modify or add treatments based on an individual's changing health condition. Further, these systems do not have an integral component whereby explanatory information is elicited from the health care provider or reviewer to facilitate analysis of the difference between actual or proposed treatment and developed treatment.

It would be a decided improvement over the prior art to have a health care management data processing system that could be used by various health care participants, including doctors, nurses, health care administrators, payor administrators, employers, and evaluators at multiple stages of the health care process. It would be a further improvement for such a system to collect information on individuals having a health concern, to guide the user to a system-selected treatment based on the information collected, and to compare an actual or proposed treatment with the system-selected treatment. The prior art systems also leave an unsatisfied need for explanatory information on differences between the actual/proposed treatment and a system-selected treatment and for obtaining systematic reviewer input as to any differences between the actual/proposed treatment and a system-selected treatment.

It would be a further improvement over the prior art for such a system to permit continuous updating and modification of the experience base, using the information input into the process for each case. For example, the information on actual treatment provided can be used to reassess the decision path for system-selected treatments.

A system implementing the above process should ideally have several qualities. It should be cost-effective, i.e., lead to reducing the total cost of health care. It should be usable in real-time, i.e., the information input into the system should be immediately processed and available for further use. It should be interactive, allowing a variety of health care participants (doctors, nurses, administrators, quality evaluators) to understand and effectively use the system. It should be flexible enough to adapt to changes in and evolution of health care professional knowledge and health care treatment methods.

A health care management data processing system designed to manage the health care process, using a data base of health care records and health condition guidelines, that includes providing diagnosis, evaluation, and utilization information, would be a decided improvement over the prior art.

SUMMARY OF THE INVENTION

To overcome these and other problems in the prior art, the present invention provides a health care management data processing system that is a real-time, interactive system to manage the health care process described above. The system can be used by hospitals, physicians, insurance companies, HMO's, and others in the health care field to promote cost-effective health care.

The present invention builds from a data base of diagnosis-based guidelines developed by medical professionals and provides a diagnosis-based system that can be used during various steps of the clinical decision process: (1) prospectively, before treatment, when an individual presents a health concern; (2) concurrently, at any stage of existing treatment; and (3) retrospectively, after treatment has been provided. The diagnosis-based guidelines are structured to work with an interactive question and answer methodology that ensures that the most appropriate data are collected and guides the user through the complex medical evaluation process. This is done by presenting questions in a logically-structured order, leading to guideline treatment option(s). The information retained by the system allows for a consistent, efficient review process. Variances between actual or proposed and guideline treatment option(s) can be used for quality assurance and audit purposes. Also, cross-specialty review is facilitated.

According to the present invention, there is provided a processing unit and software-implemented health condition diagnosis-based guidelines. A user inputs an individual's health data into a new or existing case file in response to inquiries implemented in a health-condition specific guideline. Through the interactive guideline query-response process, a guideline treatment option (or options) is obtained. The user may adopt or accept the guideline treatment option(s) or input an actual or proposed treatment that is different. Discrepancies between actual/proposed and guideline treatment option(s) are identified and the user's choice is documented through interactive queries. Once a treatment is selected, the case information is added to the data base and a reviewer can analyze the file. The case may be re-opened, and changes may be made at any stage in the process to reflect new conditions, or new or modified treatments.

BRIEF DESCRIPTION OF THE DRAWINGS

FIG. 3 is an excerpt from a diagnosis code-based index to guidelines.

FIG. 4 is an excerpt from the guideline data base, showing a guideline question and navigation structure.

FIG. 5 is another excerpt from the guideline data base, showing another guideline question and navigation structure, illustrating a path to a different guideline.

FIG. 6 is another excerpt from the guideline data base, showing a guideline question and navigation structure, illustrating how a previously selected answer can join with a current answer to identify the next step.

FIG. 7 is an example of a guideline treatment data base item.

FIG. 8 is a map of FIGS. 8A and 8B HAV.- Apr. 2, 1996.

FIGS. 8a and 8b are excerpts from the guideline procedure file, HAV.- Apr. 2, 1996.

FIG. 10 shows the medical category screen menu used to access the guidelines.

FIG. 14 shows a screen with examples of the question/answer process for utilizing the guideline for the diagnosis of thrombophlebitis.

FIG. 15 shows a screen identifying guideline treatment option(s) for a thrombophlebitis case, overlaid with a specialty review box.

FIG. 16 shows a screen identifying guideline treatment, proposed treatment, and final recommendation treatment for a thrombophlebitis case.

FIG. 17 shows a screen used for specialist review of a case exhibiting variances between proposed and guideline treatment.

FIG. 19 shows an exemplary screen of a Daily Productivity Report for an Operation Manager.

FIG. 20 shows an exemplary screen of a Daily Productivity Report for a Supervisor.

FIG. 21 shows an exemplary screen of a Daily Productivity Report for a Care Manager.

FIG. 22 shows an exemplary screen of a Daily Productivity Report for a Specialist Reviewer.

FIG. 23 shows an exemplary screen of a Daily Productivity Report for a Specialist Reviewer Productivity.

FIG. 24a shows an exemplary first page of a Specialist Review Work Sheet.

FIG. 24b shows an exemplary second page of a Specialist Review Work Sheet.

FIG. 25 shows an exemplary Volume to Physicians summary.

FIG. 26 shows an exemplary case summary for Medical Category: Cardiovascular/Respiratory FIG. 27 shows an exemplary proposed treatment summary for Medical Category: Cardiovascular/Respiratory.

FIG. 28 shows an exemplary Treatment to Cases summary for Guideline: Coronary Artery Disease.

FIG. 29 shows an exemplary Treatment to Cases summary for Guideline: Coronary Artery Disease.

FIG. 30 shows an exemplary Treatment and Resources Impact to Guideline summary.

DETAILED DESCRIPTION OF THE PREFERRED EMBODIMENT

A. Hardware/Software System Overview

Figures 1, 2, 2A, 2B:
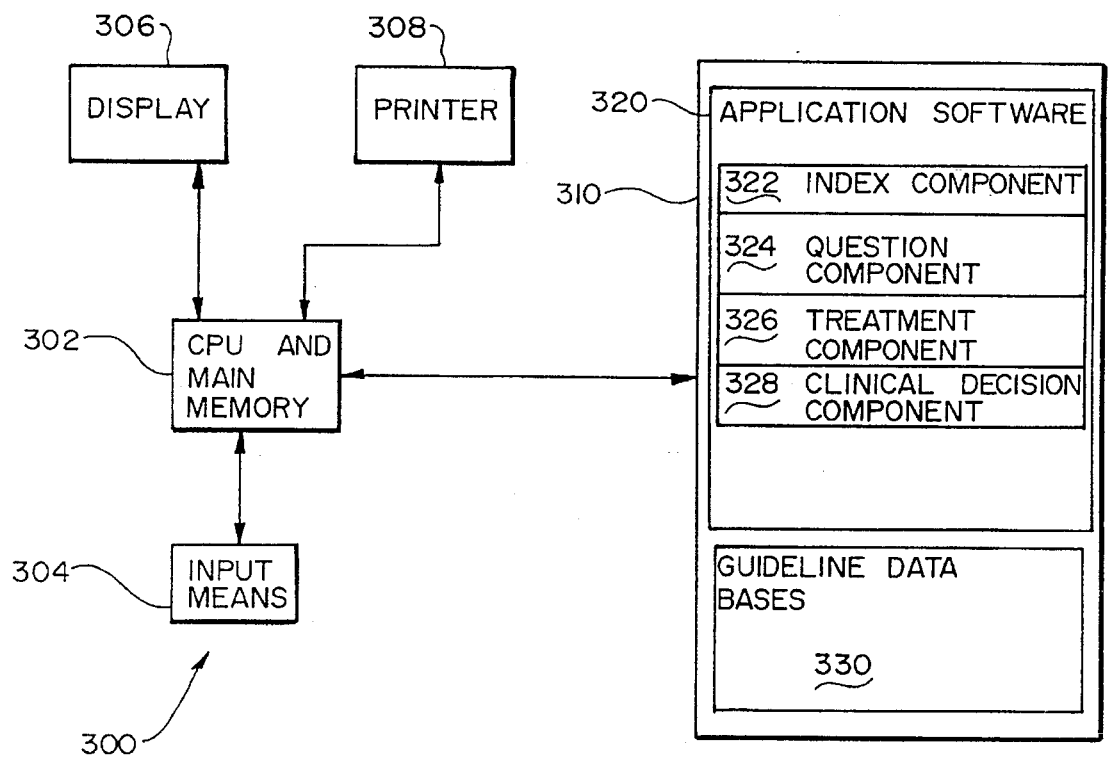
FIG. 1 is a block diagram of the system of the present invention.
FIG. 2 is a map of FIGS. 2A and 2B from a medical category index to the guideline data base.
FIGS. 2a and 2b are excerpts.

The present system is shown in general block-diagram form in FIG. 1. As seen there, the system 300 comprises a processing unit or CPU with main memory 302; input means 304, such as a keyboard connected to the CPU/main memory 302; and two output devices, a display 306 (such as a CRT or other screen device) and a printer 308, also connected to CPU/main memory. Storage device 310 (e.g., a disk drive) communicates with the CPU/main memory 302 and is the memory unit for storing application software 320 and guideline data bases 330. The system 300 also includes appropriate operating system software (not shown).

The preferred implementation platform of the present invention is a system implemented on an IBM compatible personal computer having at least four megabytes of main memory and an eighty megabyte hard disk drive, with Microsoft Windows as the user interface and Paradox as the data base management software. Individual personal computers can be networked to give multiple users access to a common data base. The application software 320 is written in Microsoft C development language. The application software 320 functions as an interactive presentation tool, permitting the user to interactively exchange information with the system 300. Certain session data are recorded to allow case audit and analysis of system use.

At the foundation of the system 300 is a set of diagnosis-based guidelines that are derived from medical professional and health care management expertise. Each guideline is associated with a particular health care condition for which treatment exists. Each guideline is intended to lead a system user through a sequence of interactive data-collection queries based on the specified health care condition observed in an individual patient. The data-collection queries are logically structured so that the guideline user identifies pertinent patient characteristics and is led to an endpoint that is usually one guideline treatment option. However, the endpoint may also be two or more alternative treatments, a pointer to a different guideline or a recommendation for further clinical evaluation before treatment is selected.

As implemented in the system 300, a guideline can be viewed as a decision tree with multiple data collection nodes, most of which have conditional branching to connected nodes based on user-supplied data. The endpoints of navigation through the decision tree are usually embodied in a set of treatment options. The path to any treatment option involves one or more conditional branches. Thus, each guideline implemented in the system 300 has a definite algorithmic structure that guides the user. The structure and content of and process for development of guidelines are discussed in greater detail below.

The system 300 presents each guideline in a questioning logic sequence where the response to each question drives to the next question or to the appropriate treatment option(s). As defined in the present invention, a treatment option includes an intervention and the corresponding primary health care resources utilized in that intervention. The data for implementing a guideline include, in addition to question text, the presentation parameters, such as the presentation order for the questions and the conditional branching logic that is driven by the user's responses to the guideline questions. With each guideline implemented as a set of data base parameters, the application software is designed as a shell used to access and present the guideline content and control the navigation through the questioning process.

Once the user reaches one or more guideline treatment options, the system 300 elicits from the user information identifying the actual treatment already given or, preferably, the treatment proposed for the individual that presented the health care condition. The system 300 compares the actual or proposed treatment against the guideline treatment option(s). This comparison addresses not only the intervention or procedure that is central to each treatment option but also the several health care resource parameters that are part of each treatment option (and are discussed in greater detail below). The system 300 develops a treatment evaluation based on the comparison to identify discrepancies between the guideline treatment option and the actual or proposed treatment. Following this evaluation, the user enters a final recommendation treatment. If this final recommendation treatment differs from the guideline treatment option previously displayed, the system 300 elicits information on the reasons for the difference(s) found in the system's comparison of the two.

There are four general components to the application software 320: (1) an index component that facilitates quick access to the correct guideline 322; (2) a question component that presents the questions and controls navigation through the guideline based on the user's responses 324; (3) a treatment component that presents the guideline treatment options, and highlights the guideline-selected option(s) based on user responses to questions 326; and (4) the clinical decision component that facilitates the collection of data to support analysis of the use and impact of the guidelines and the tracking of guideline activity by case 328.

The index component utilizes several different data bases. The main index data base, a portion of which is shown in FIG. 2, includes: a field 10 with two digit numbers that identify one or more medical categories; a field 11 containing a textual description for each medical category; a field 12 containing two digit numbers, each of which identifies one of multiple guidelines within a medical category; a field 13 for a guideline extension identifier, signifying that certain guidelines are an extension of other guidelines; and a field 14 containing textual description for each guideline. Therefore, each guideline can be identified by a five digit number: a two digit medical category number, a two digit guideline number, and a one character extension identifier (optional). For example, the Thrombophlebitis; Extension guideline 15 is identified as 53(23X).

The diagnosis code index, a portion of which is shown in FIG. 3, cross-references each guideline number in field 16 with one or more diagnosis codes in field 17. This data base is an index used to identify a guideline based on a diagnosis code entered by the user.

The question component also has a data base. FIG. 4 shows a portion of the question and navigation data base. For each guideline identified by numbers in field 18, there are one or more questions, each identified by number and text in field 19. Associated with each question in one or more of columns 20, 21, 22 is coded navigation information identifying the next step, which may be an additional question, a different guideline or a treatment. Different paths through the guideline are indicated by codes representing each possible answer provided by the user. A two digit code in column 20 or 21, such as the "02" at 23a, identifies the next question to be answered. Two characters, at least one of which is a letter, such as the "4A" at 23b, identifies a treatment. Column 20 shows the code for the next step when the user response to a question is "Pass" (or "yes"). Column 21 shows the code for the next step when the user response to a question is "Fail" (or "no"). Column 22 contains information identifying a preceding question and its responses, if the path from a question depends on the user responses to both the current and a preceding question. (An example of this appears in FIG. 6 and is explained below.) FIG. 5 shows another exemplary portion of the question and navigation data base. As shown in FIG. 5, a four digit code 24 in column 20 (or 21) identifies when another guideline should be applied as the next step.

In implementing a guideline, the question/answer combinations are sequenced to yield the most efficient route to a treatment. Also, the question/answer combinations are sequenced based on frequency of use, listing the most common questions first. This sequencing scheme makes the present invention more efficient in moving the user directly to the guideline treatment option(s) and collecting only relevant information.

FIG. 6, which shows a further exemplary portion of the question and navigation data base, provides an example in which the answer to a preceding question together with the answer to the current question defines the next step. Question/answer 04g under guideline 53(03) is illustrative. Under the column 22, labeled "Frm", it is shown that question/answer 04g could have been reached by previously answering question 02 as Pass (code "02P") or by selecting any of answers "a" through "f" to question 03 (codes "03a" to "03f"). If 02P or 03a through 03e were chosen as the previous answer and response "g" is selected for question 04, then in each case the next step is the treatment options of "2A" or "2C". However, if response "g" were selected to question 04 after the answer corresponding to code "03f" was selected, then the next step is "PR," indicating physician review.

The treatment component also uses data bases. FIG. 7 is an example of a guideline treatment data base set for the condition corresponding to guideline 53(23). In general, for each guideline identified by a five digit number in field 25, there are listed one or more treatment options. Each treatment is identified by: a two character treatment code in field 26, a textual treatment description in field 27, and several resource utilization indicators in columns 28-32, labelled Setting, A/S, LOS, Preop LOS, and Flag, respectively. (These resource utilization indicators are explained in greater detail below.) Also, a numeric procedure code, such as a Current Procedure Terminology (CPT) code, is provided in field 33.

A complete menu of all treatments that may be referenced in any guideline, including treatment descriptions and resource indicators, is retained in a procedure file that is used by all guidelines. The procedure file, an excerpt of which is shown in FIG. 8, lists the numeric procedure code in field 34, the five resource utilization indicators in fields 35-39, and numeric procedure description text in field 41. A count of the number of text lines in the numeric procedure description is kept in field 40.

The clinical decision data collection component is linked to the previous three components to collect data and track-guideline activity. Its purpose is to provide a foundation for moving from the individual cases processed in the system to aggregated statistics for a set of cases. The reports facilitated by this component are discussed below.

B. Description of a Diagnosis-Based Guideline

Diagnosis-based guidelines provide a framework to reflect the critical factors in the clinical decision process usually leading to treatment, to define optimal resource allocation, and to outline key patient data. A guideline is not a fixed formula or cookbook, although it must be a definite, step by step algorithm that can be coded; rather, a guideline presents a disciplined framework or process to guide and assist the user, such as a health care provider, in identifying appropriate treatment.

Application of a guideline to an individual's health condition in the present system 300 consists of four phases: (1) the entry phase; (2) the question/data collection phase; (3) the assessment phase; and (4) the final recommendation phase. In the entry phase, the guideline to be applied is identified. Generally, a guideline is identified by a recognized health condition description, which may be stated as a symptom or a diagnosis.

Once the desired guideline is identified among those available in the system, the question/data collection phase begins and the user is presented with a series of questions. The guideline questions are organized in a format similar to a decision tree or flow chart. Generally, the next question is identified based on the answer to the current question. However, some questions elements may be designed only to elicit information and the answer does not (at least immediately) influence the next question presented. The number of questions presented in a given case varies with the guideline selected and the answers to the questions presented.

In the third phase, the guideline identifies a treatment option or other action, based on the user's answers to the questions presented. As noted previously and shown in FIGS. 7 and 8, a treatment option consists of a textual description, a numeric procedure code, and resource utilization indicators.

There are a five resource utilization indicators. "Setting" identifies whether the treatment occurs in an inpatient facility (IP), outpatient facility (OP), or physician office (OF). "LOS" (Length of Stay) identifies the number of days for inpatient facilities. "A/S" (Assistant Surgeon) designates whether an assistant surgeon is required. "Preop LOS" (Preoperative Length of Stay) designates the number of inpatient days required prior to elective surgery. "Flag" indicates special considerations such as large case management, physician review, or coordination of services.

More than one treatment option may be provided as the outcome of a guideline. Also, a treatment may not be provided; rather, application of a new guideline or the option of further clinical evaluation is indicated.

As noted above, a guideline is not a fixed formula that, in effect, requires the user to pursue a given treatment. To the contrary, use of a guideline in the present system 300, specifically contemplates that the user may select and enter into the system a proposed or actual treatment that is not the treatment option indicated by the guideline. If the user selects a proposed or actual treatment that is not the treatment option indicated by the guideline, then the system calls for specialist review of the case. This usually involves seeking the opinion of a person different from the person that selected the proposed or actual treatment. Once the specialist review is completed, the user enters into the system a final recommendation treatment. This can be the guideline treatment option, the proposed or actual treatment previously entered by the user, or a different treatment resulting from the specialist review.

A primary purpose of the guidelines is to initiate and facilitate comparison and evaluation, if there is a difference between the final recommendation treatment and guideline treatment option or between the final recommendation treatment and proposed/actual treatment. This comparison and evaluation occurs in the fourth phase. If there is a difference between the final recommendation treatment and guideline treatment option, the system 300 elicits an explanation for each variance in the intervention or procedure, as well as in resource utilization indicators (provided that the differences in the intervention or procedure permit meaningful comparisons). If there is a difference between the final recommendation treatment and proposed/actual treatment, e.g., the user is overriding the proposed/actual treatment of a provider, the system 300 elicits comments on the influence of the guideline process on the care plan, i.e., the manner in which care changed as a result of the guideline process.

The content of a guideline requires that it reflect accepted clinical practice when formulated and also requires: (a) ongoing evaluation to ensure appropriateness; and (b) assessment of its implementation to ensure consistent application and appropriate sensitivity and specificity of its contents. The clinical content of each guideline needs to be based on available evidence and refined by result of application. Thus, guidelines are developed first as diagnosis and treatment models by health care professionals and these models are refined to sufficient definiteness to permit their coding.

Figure 9A:
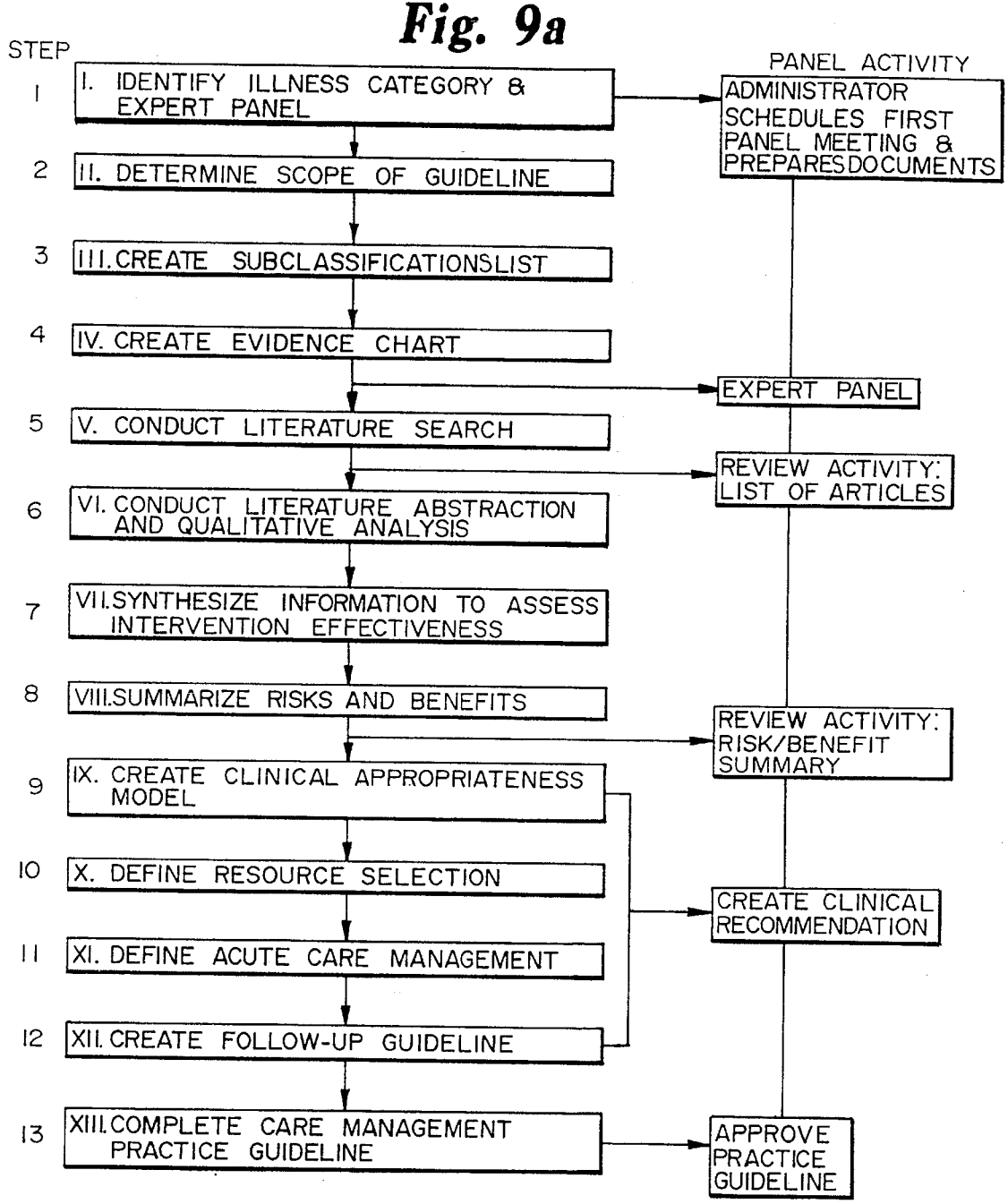
FIG. 9a is a flow chart of the guideline development process.

FIG. 9a is a chart outlining the guideline development process. At step 1 the illness category that the guideline will cover is identified. This decision is usually based on existing patterns, such as the volume of cases for an illness category, the extent of variations in treating an illness, or cost for treating an illness. A panel of people with expertise in the selected illness category or in research procedures is established.

At step 2, the scope, i.e., components of care, of the guideline is identified. The four major components that a guideline may include are diagnostic guideline, therapeutic selection, resource selection and acute care management. The care components decision is based on the purposes for developing the guideline, understanding how it would be implemented, and the financial resources available for guideline development.

At step 3, any subclassifications used to identify severity levels of the illness with a set of treatment options are identified. The subclassifications should be standard groupings whenever possible, so they will be consistent with data used in future analyses.

At step 4, an evidence chart that defines aspects of the diagnosis or treatment which require specific scientific support or evidence is developed. This evidence is necessary to determine the impact on expected clinical outcomes of a specific intervention. It also describes potential adverse affects or outcomes and complications which will need to be considered in evaluating overall risks and benefits.

At step 5, a literature search is conducted. Prior to conducting the literature search it is important to define the search logic, process, and list of exclusions in order to efficiently expend time and resources. The evidence chart helps organize the information to complete the literature search.

At step 6, evidence retrieved for each linkage of the evidence chart is documented in a standard format. The data abstraction process is completed. The results are summarized to specifically document the results of each study.

At step 7, quantitative analysis is used to draw conclusions about a particular intervention's effectiveness. Narrative summaries are created of the information for each intervention, describing the impact on expected outcome. This synthesis of information, including the narrative summary, is provided to knowledge experts for a decision of clinical impact of intervention on expected outcome.

At step 8, a summary of the risks and benefits of interventions appropriate to a diagnosis is generated. This summary may include positive outcome, grade of impact, contraindication, adverse affect/mortality, adverse affect/ morbidity, disability, discomfort and cost impact. At this point a meeting of the expert panel occurs. During this meeting the risk summary benefit is reviewed, resource selection, key management and follow-up guidelines are defined, and consensus on the guideline is reached.

At step 9, a clinical appropriateness model is created by the panel that describes by intervention: patient characteristics for which the intervention is indicated and contraindications, with appropriate alternative when present. This information is then aggregated into a guideline.

At step 10, for each intervention adopted into the guideline, the panel determines a minimum level of resource required to administer the treatment. This includes evaluating the setting, assistant surgeon requirement and potential variables affecting resources.

At step 11, acute care management is defined. For each intervention requiring an inpatient stay, the panel determines the appropriate length of stay including preoperative days.

At step 12, following completion of a guideline, the panel develops guidelines for extended care, which include the indications, treatments and related resources.

At step 13, the panel reviews the entire guideline for clarity and accuracy. Panel members vote formally for adoption of each guideline.

Guidelines are continuously updated by recurring searches by diagnosis for new findings and studies. Also each guideline can be reviewed on a periodic basis, such as annually. Information from the care management system can be retrieved for that review, including results of use, frequency of use, frequency of variation by component, type of variations. Because the present invention implements the guidelines as data base parameters, the system is flexible; it can be readily adapted to changes in and evolution of health care professional knowledge and treatment methods.

C. Using the System

Figure 9B:
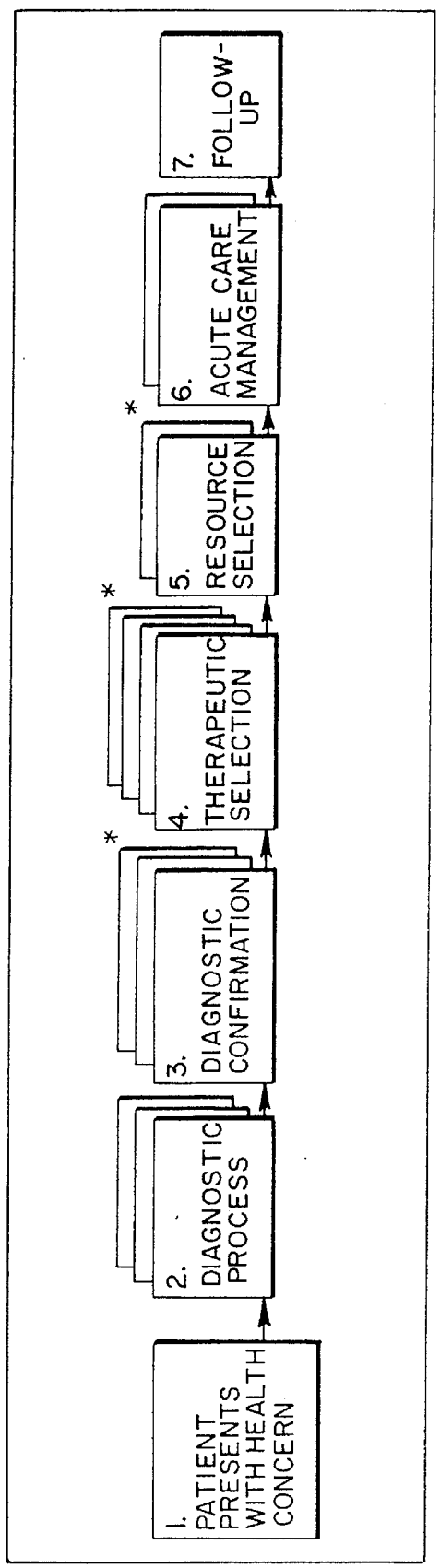
FIG. 9b is a flow chart of the clinical decision process.

FIG. 9b shows the basic steps of the clinical decision process in which the present invention may be used. Initially, an individual presents a health condition to a provider. Next, the diagnosis process is initiated. The health care provider or other user collects information from the individual and performs tests or other procedures. At this point, the system user (whether it is the provider, assistant, administrator, or other) may initiate the guideline process leading to a treatment option. Also at this point, the user may input an actual or proposed treatment prior to initiating the guideline process.

Broadly viewed in terms of the clinical decision model of FIG. 9b, the system 300 can be used to aid diagnostic confirmation and therapeutic selection associated with the diagnosis. The system 300 can also aid resource selection, because the guidelines used in the system-contain resource recommendation parameters. Thus, the guidelines address both the problem of overutilization and its resulting direct costs and underutilization, which lowers the quality of care and usually leads to indirect costs. Using the system in real-time to guide proposed care allows care plans to be changed and provides a clinically-sound basis for ongoing quality and outcomes analysis through tracking a specific diagnosis. Potentially inappropriate or less-than-optimal care can be identified and corrected. The guideline structure provides a basis for consistent derision-making, while allowing flexibility for complex cases requiring care coordination and intensive review.

To illustrate how the system 300 aids diagnostic confirmation, therapeutic selection and resource selection, it is useful to trace the actual process followed by a system user, including the screens presented.

1. Initiating a Guideline Process - Accessing the Desired Guideline

Access to the appropriate guideline in a real time mode is a key feature of the present invention. Therefore, the index component is structured to allow the user a method of locating the appropriate guideline with differing levels of information. For example, the guidelines are diagnosis-based (that is, they address a specified health condition that has been recognized), but the user (clinical reviewer) may only know the procedure being proposed. This requires an efficient search of all of the guidelines that contain that procedure in order to identify the correct guideline for review of the case.

Figure 11:
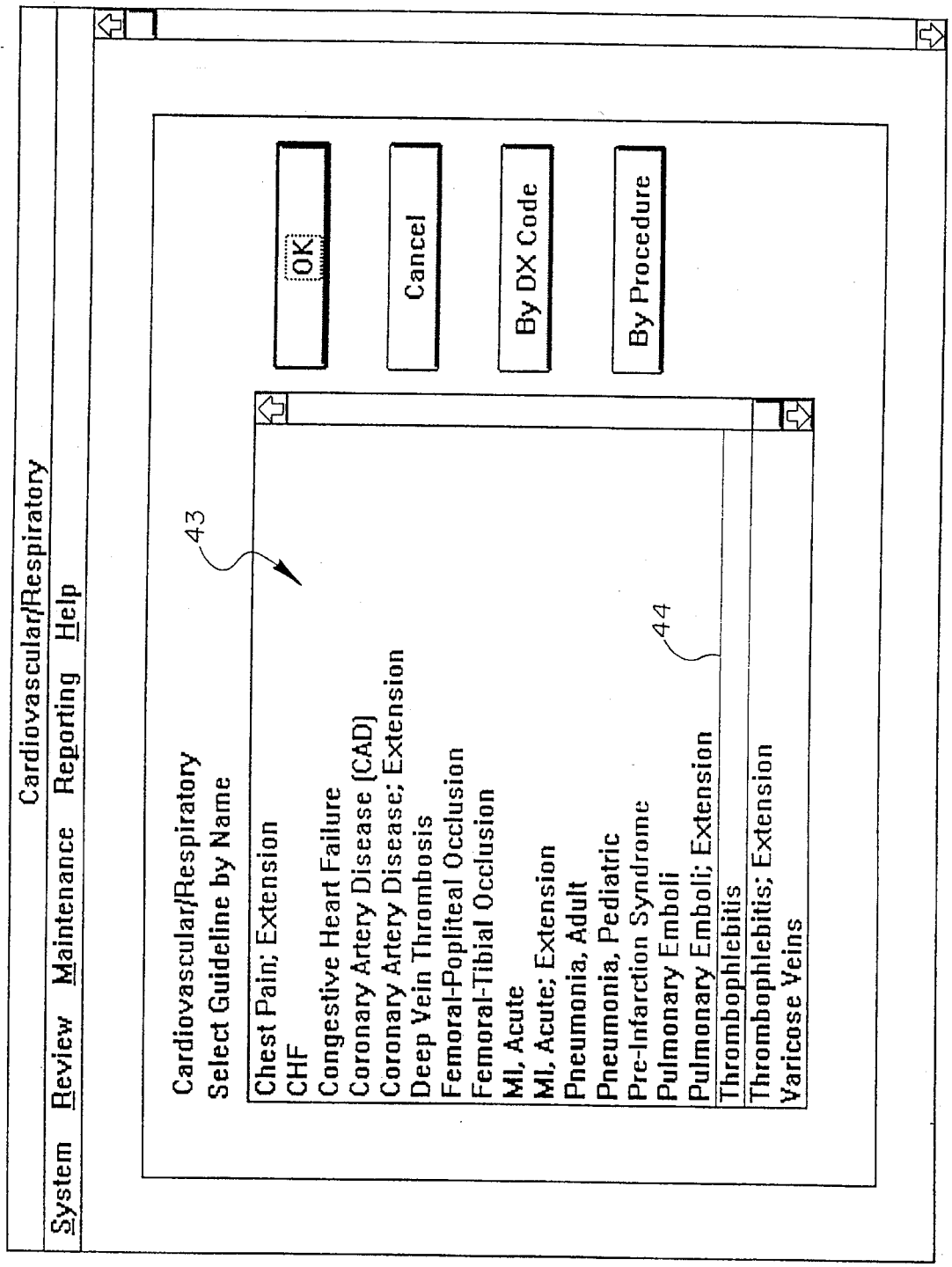
FIG. 11 shows a screen listing of titles of some of the guidelines for selected medical conditions within the cardiovascular/respiratory medical category.

There are three ways the user may initiate the guideline process. First, the user may select one category from an alpha index of predefined medical categories, as shown in the screen depicted in FIG. 10. Each category leads to an alpha index of guideline titles within that category, each title representing a health condition or diagnosis, as shown in FIG. 11. This facilitates quick access to the desired guideline. More than one description may exist for a guideline. To actually select a guideline, the user first selects one category from a medical category list 42 as shown in FIG. 10. For each selected medical category, the system 300 next presents a menu of guideline titles 43 as shown in FIG. 11. The user then selects the desired guideline 44, which is highlighted as shown in FIG. 11.

Figure 12A:
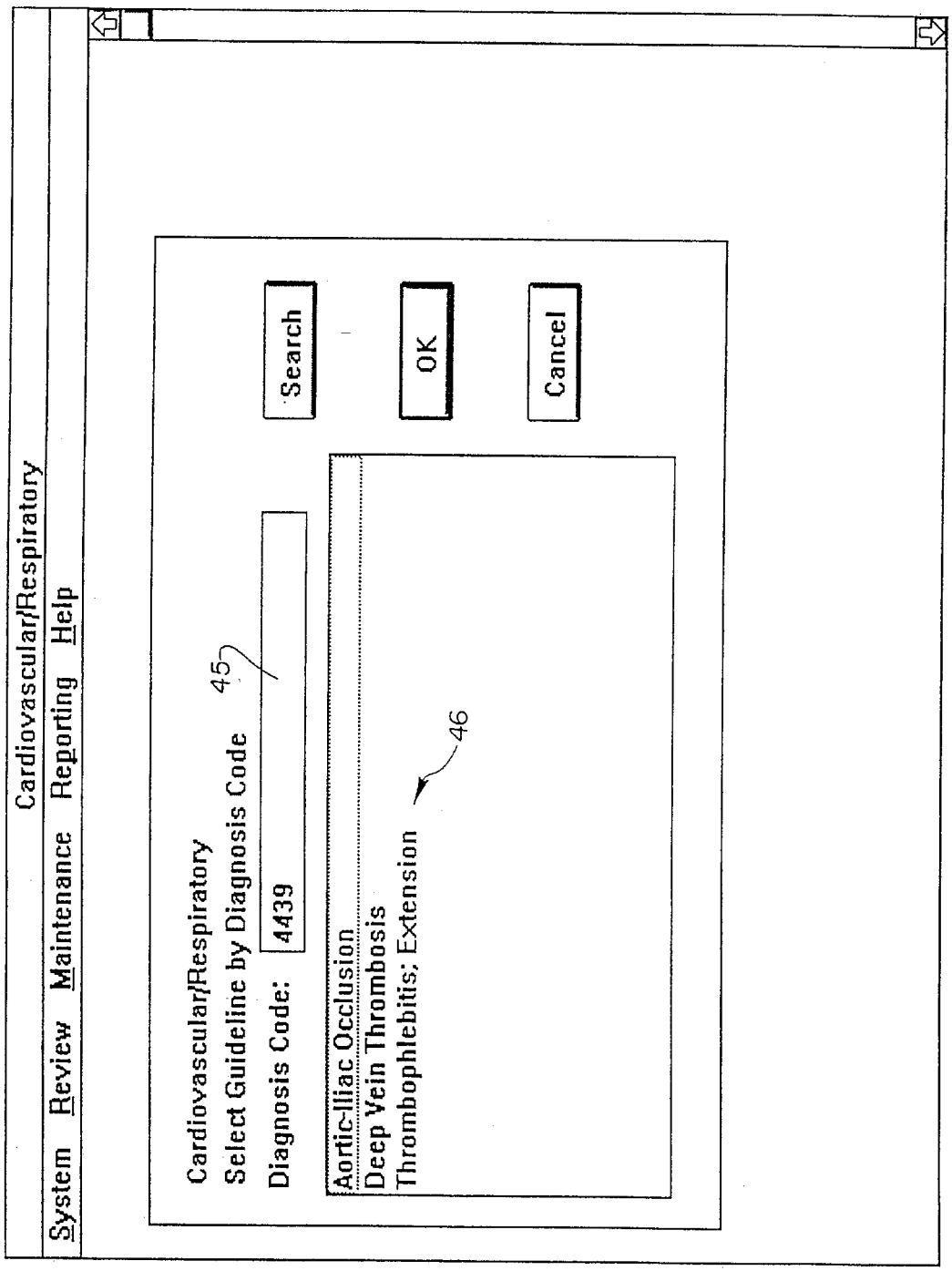
FIG. 12a shows a screen used to access guidelines by diagnosis code.

The guideline process may also be initiated a second way. Once a medical category is selected, the user may move to a screen for imputing a predefined diagnosis code, as shown in FIG. 12a. For example, in the preferred embodiment, a code from the International Classification of Diseases, 9th Revision, Clinical Modification, or ICD-9-CM, a standard coding system, may be entered in field 45. One guideline may cover a range of diagnosis codes and a diagnosis code may identify more than one guideline. The user selects the desired guideline from the relatively short menu 46 generated for the given diagnosis code. Entry of a 3 digit code will cause the system to display a list of all of the guidelines containing that diagnosis code. No diagnosis code validation is done. (Note that although the ICD-9-CM code is 5 digits, only the first 3 are used to index.)

Figure 12B:
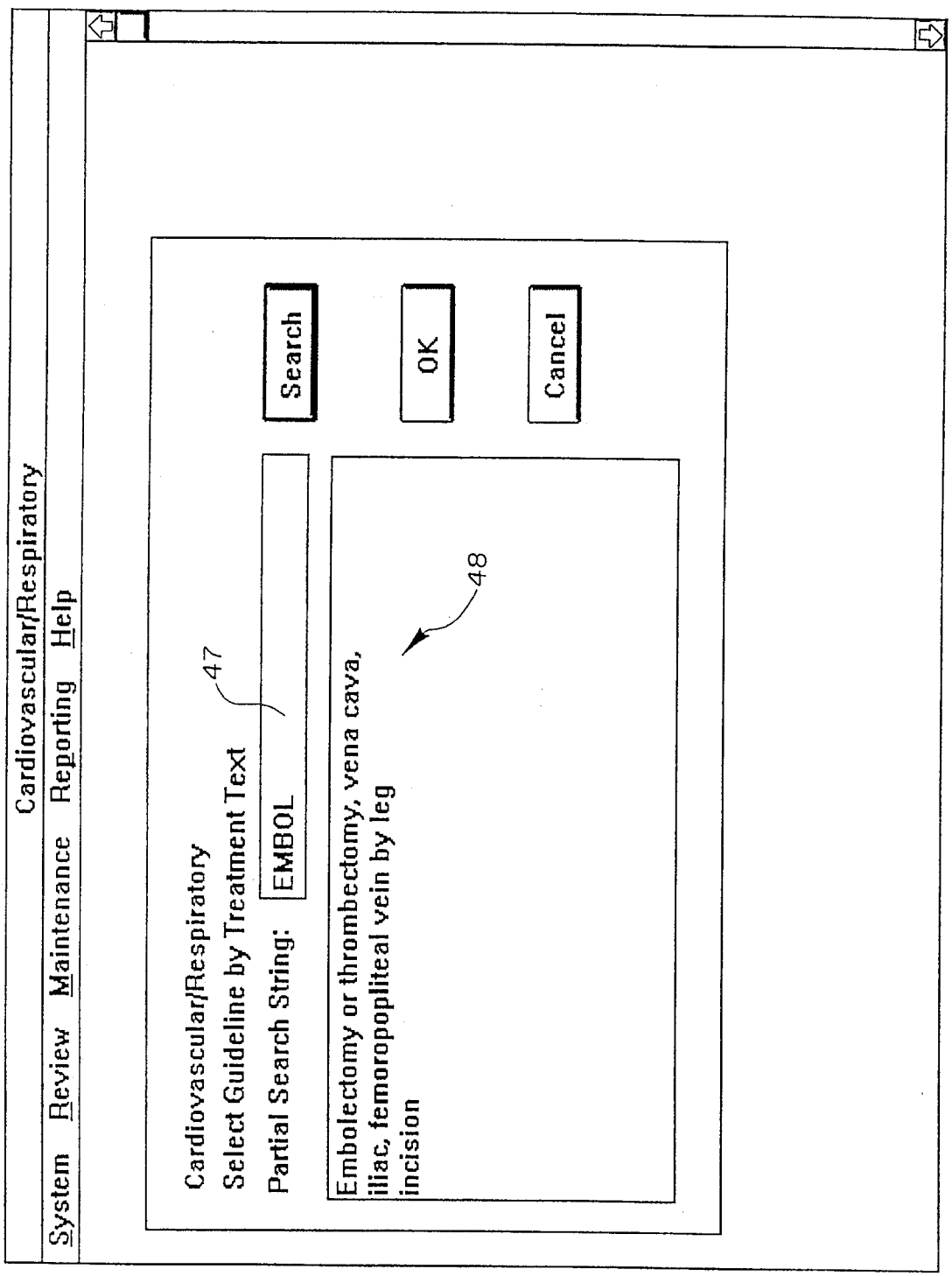
FIG. 12b shows a screen used to access guidelines by treatment text.

The guideline process may also be initiated without identifying a diagnosis. As shown in FIG. 12b, the user may input text representing a known or proposed treatment or procedure information in field 47. A procedure or treatment may be found in more than one guideline. Selection is by alpha description, allowing for a partial string search of 5 characters into the index list. The procedure descriptions contain the most significant characters first to allow a fixed position search. The search is limited to procedure code descriptions only, excluding complication descriptions and notes. If matching text is found, the treatments containing that text are identified. The user selects the desired treatment from menu 48. From that, the guideline(s) containing the identified treatment is located. Therefore, it is possible that treatment text can lead to more than one guideline. The user then selects the desired guideline from a menu generated in response to the treatment text selected.

Figure 13:
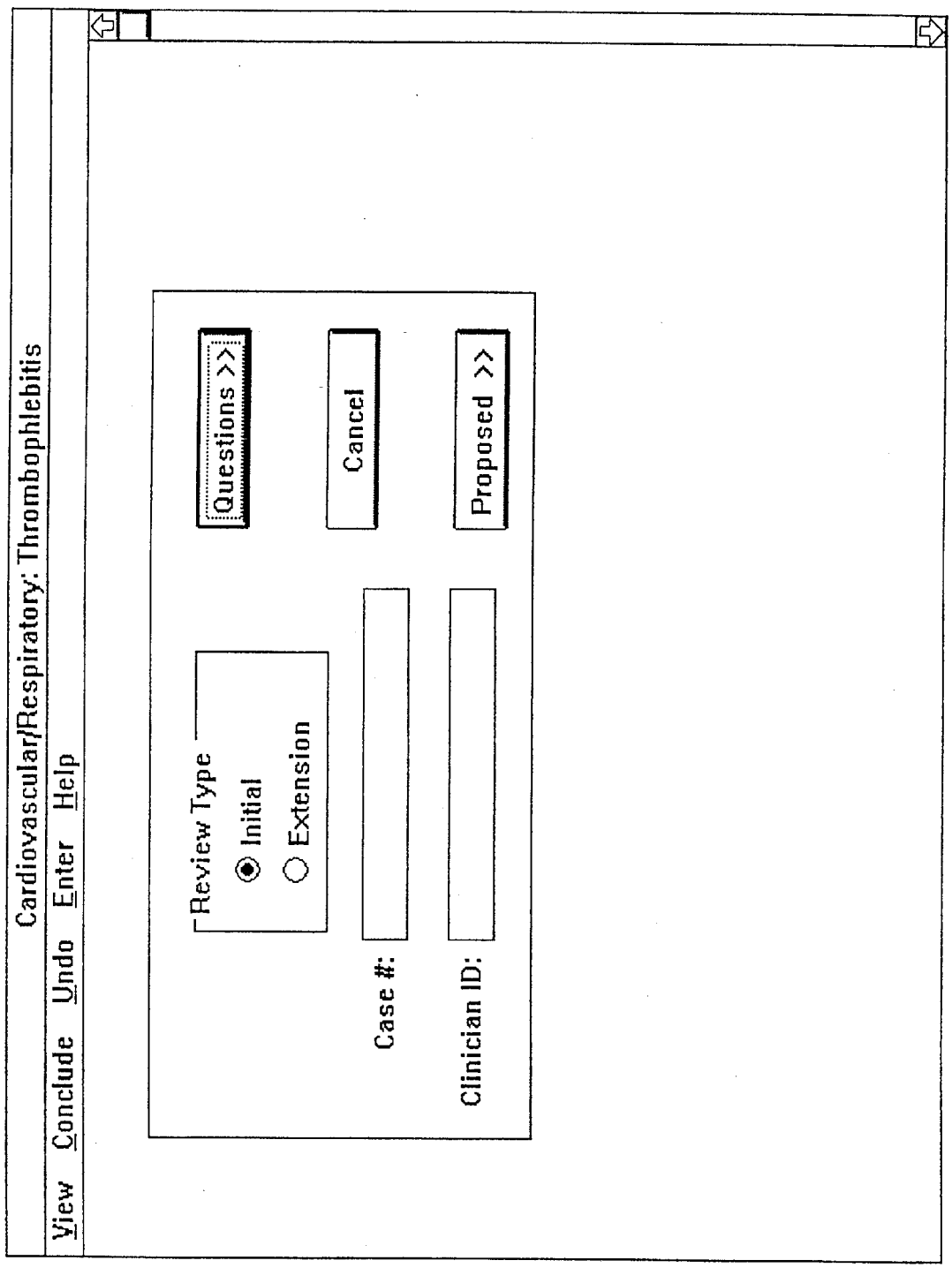
FIG. 13 shows a screen used to open a guideline process after guideline selection.

After a guideline is selected, the software calls for identification information to be provided by the user. This is shown in the screen depicted in FIG. 13. First, the type of review or file is identified. Review type is either initial or extension. Extension review is entered after an initial guideline is used. The extension may be caused by a delayed response or condition in the individual, a complication, a failure of initial treatment, or other reason. (An extension guideline is used, if available.) Next, a case identification number is entered. It is important that a patient have a unique identification number for each admission to ensure all information on the patient is in a single file. As discussed above, extension review allows the user to add information to an existing file. A clinician or care provider identification number is also entered. Each clinician should be identified by a unique number.

2. Navigating through a Guideline - the Question/Data Collection Phase

Once a guideline is selected, the user proceeds through an interactive process of questions and answers to reach a treatment option. An example screen showing part of the process is depicted in FIG. 14. Several questions are displayed and a first question 49 is presented to the user by highlighting. There are three question formats. First, the question can be in narrative form as at 49 and require a "pass" or "fail" (corresponding to yes or no, respectively) answer 50. The answer is selected by "pushing" a displayed "button". Second, the question may offer multiple answers as at 52 and permit selection of only a single answer. Response navigation is attached to each multiple-choice selection (only pass applies). Third, the question may provide multiple selections as at 51 and all applicable selections may be chosen. The third type of question is for both navigation and data collection, and some selections made do not affect subsequent questions. All questions are presented by highlighting the current question, and as many questions as possible are displayed on one screen. Questions are numbered to permit tracking the clinical pathway used to arrive at a treatment option. A question and any of the responses may extend over more than one line.

Based on the user's answer to the initial question, another question is presented, but it may not be the next question in the number sequence. Navigation among questions is dependent on answers and some questions may be skipped. Therefore, the user enters only relevant data and does not have to sift through unnecessary or irrelevant questions. No backward navigation is allowed in the questioning logic. However, the user may back up to erase and re-enter responses. The number of questions presented to the user varies depending upon the guideline selected and answers provided.

A question may be arrived at by multiple paths. For example, if question 3 is arrived at from question 1 or 2, then there could be 2 sets of pass/fail navigational options. Ultimately, after navigating through a guideline, the user will be provided with at least one treatment option, a new guideline or instructions to seek further clinical evaluation. If questioning determines the need to utilize a different guideline, then the user is either transferred directly to the new guideline and/or a message is displayed. A given combination of answers may lead to multiple treatment options, as shown by the two highlighted treatments 53, 54 in the screen depicted in FIG. 15.

Codes are stored that indicate the path taken through the questioning process (clinical pathway). A "help" menu accessed by a function key is available at any time to further clarify the question, treatment, or list of references. Using the pull-down menu "view" accessed as indicated 56 in FIG. 14, the user may review answers to previous questions. However, except in the non-directive mode described below, the user may not work backward or select questions in an arbitrary manner. Due to the navigational control built into a guideline, only relevant questions that are required to reach a treatment option are presented and answered. The user has the ability to exit and suspend review at any time. The review status is stored and the user may continue the review at a later time.

3. Treatment and Review

The guideline question sequence will lead to one or more guideline treatment options, a new guideline, or suggest further clinical evaluation. As shown in FIG. 16, all treatment options are displayed to the user with the guideline-selected treatment(s) highlighted. Multiple treatments may be appropriate for a specified combination of answers. A treatment option may be displayed with message or note lines. More than one page of treatments may be present, and the user can page through all treatments.

A treatment option is displayed in eight fields, as shown in the screen depicted in FIG. 16. The first field 57 is a two-character treatment code that facilitates tracking of treatments within a guideline. The code is unique within the selected guideline only. Next is a field 58 containing a brief description of the treatment, followed by a field 59 for the applicable numeric procedure code. Multiple procedure codes may be present if a treatment consists of more than one procedure. A procedure code may not always be available for a treatment option. If it is not available, an internal code will be created but not displayed on the screen. The procedure code can be used in reimbursement for the selected treatment.

Next the resource utilization indicators are listed. The treatment setting field 60, labelled, "Setting", identifies inpatient facility (IP), outpatient facility (OP), or physician office (OF). The length of stay field 61, labelled "LOS", provides the number of days for inpatient facilities. The assistant surgeon field 62, labelled "A/S", designates whether an assistant surgeon is required (y=yes; n=no; s=standby). The preoperative days field 63, labelled, "Preop", designates the number of inpatient days required prior to elective surgery. Flag field 64 indicates special considerations such as large case management, physician review, or coordination of services.

As stated previously, the user may enter an actual or proposed treatment prior to or after obtaining the guideline treatment options. To enter an actual/proposed treatment after arriving at a guideline treatment option, the user utilizes the "Enter" menu and reaches a screen with the format shown in FIG. 16. As shown in FIG. 16, for the proposed/actual treatment the user enters information in five labelled fields, including treatment code 69 and the resource utilization indicators of Treatment Setting 65, Length of Stay 66, Preoperative Days 67, and Assistant Surgeon 68. The user normally enters a 2-character treatment code corresponding to one of the treatment options listed above fields 65–69. If the proposed/actual treatment is not listed in that guideline, then a reserved code will be entered and the proposed/actual treatment must be described.

If the proposed/actual treatment, including resource utilization indicators, is not the same as the guideline treatment option, then the system prompts the user to initiate specialist review. FIG. 17 shows a screen used in the specialist review process. The specialist review window is overlaid on the treatment options list screen. The following fields have data automatically entered: case ID number 70, review ID number 71, and specialist review number 72. A five-character ID field 73 is user-filled to identify the specialist reviewer. Four types of review with differing associated costs and expertise can be selected: clinical review (CR) 74; physician review (PR) 75; independent medical exam (TIME) 76; and appeal 77. Clinical review is conducted by a licensed professional with expertise in a particular specialty including the provider or another on the user staff who has the authority to approve variances. Physician review is by a consulting physician with authority to approve variances. TIME is a required referral for a second opinion examination. This type of review is chosen based on individual case merits or for a mandatory second opinion list. Appeal is a review by a consulting physician generated by an appeals notification.

The reason field in the specialist review window includes seven possible reasons why the case was carried to a different level of review, including appropriate treatment plan 78, partial procedure 79, setting 80, LOS 81, preop days 82, assistant surgeon use 83, and diagnosis confirmation 84. For any given case, multiple reasons could be present. Any variances between the proposed/actual treatment, including resource utilization indicators, and guideline treatment option are automatically designated. Actual consideration of the case by a specialist reviewer occurs off-line. The result of that review is communicated to the user, who now enters a final recommendation, incorporating the conclusions reached in specialist review, in the format required by the screen shown in FIG. 16.

With a guideline treatment option identified and a user-selected proposed/actual treatment as well as a final recommended treatment entered in the system-defined format, the system 300 performs comparisons.

Whenever there is a variance between the treatment or a resource utilization indicator for a final recommended treatment and guideline treatment option, the system elicits reasons for the variance(s). The "reason" field corresponding to a treatment or resource utilization indicator where there is a variance is highlighted. One character standard reason codes are used to explain overriding (typically, by exceeding) the guideline treatment option. Reason codes include the following:

A - additional diagnosis (comorbidity)
B - significant clinical findings
C - complication
D - unavailable information
E - alternative care availability
F - facility capability
G - geographic distance
H - social situation
I - surgical stabilization
J - contraindication
K - age
L - practitioner experience
M - patient preference
O - system override
Z - other For example, "Setting" reason must be completed if the final recommendation treatment Setting is higher than the guideline treatment Setting (IP>OP>OF). "LOS" reason must be completed if the final recommendation LOS is greater than the guideline LOS. "Preop" reason must be completed if the final recommendation Preop days are greater than the guideline Preop days. Assistant Surgeon reason must be completed if the final recommendation Assistant Surgeon use is greater than the guideline Assistant Surgeon (Y>S>N). Diagnosis confirmation reason must be completed if a specialist review reason indicates diagnosis confirmation.

A final recommendation reason description is entered if there is no standard reason code for the final recommendation treatment or for further explanation even when a standard code exists. For example, it is desirable to elicit user comment identifying other diagnosis information that was considered relevant to treatment selection. Such information may lead to future modification of the guideline. A pull-down menu allows access to a free text entry window for comments.

The "Care Changed" fields are used if the final recommendation treatment is different from the proposed/actual treatment. Whenever there is a variance between the treatment or a resource utilization indicator for a final recommendation treatment and actual/proposed treatment, the system elicits an indicator of whether the final recommendation treatment affected the actual care plan. The "care changed" field corresponding to treatment or a resource utilization indicator where there is a variance is highlighted. The treating physician indicates whether the care plan changed based on the recommendation (Y, N, or U=Unknown). Setting "Care Changed" is used if the final recommendation treatment Setting is different than actual/proposed Treatment Setting. The treating physician indicates whether the care plan changed based on the final recommendation (Y, N or U). LOS "Care Changed" is used if the final recommendation LOS is different than the actual/proposed LOS. The treating physician indicates whether the care plan changed based on the final recommendation (Y, N or U). Preop "Care Changed" is used if the final recommendation Preop days is different than the actual/proposed Preop days. The treating physician indicates whether the care plan changed based on the final recommendation (Y, N or U). Assistant Surgeon "Care Changed" is used if the final recommendation Assistant Surgeon is different than the actual/proposed Assistant Surgeon. The treating physician indicates whether the care plan changed based on the final recommendation (Y, N or U). DX "Care Changed" is used if the case was sent to specialty review for diagnosis confirmation, then the treating physician annotates whether he agrees with the decision (Y, N or U).

D. An Example Guideline - Thrombophlebitis

Figure 18:
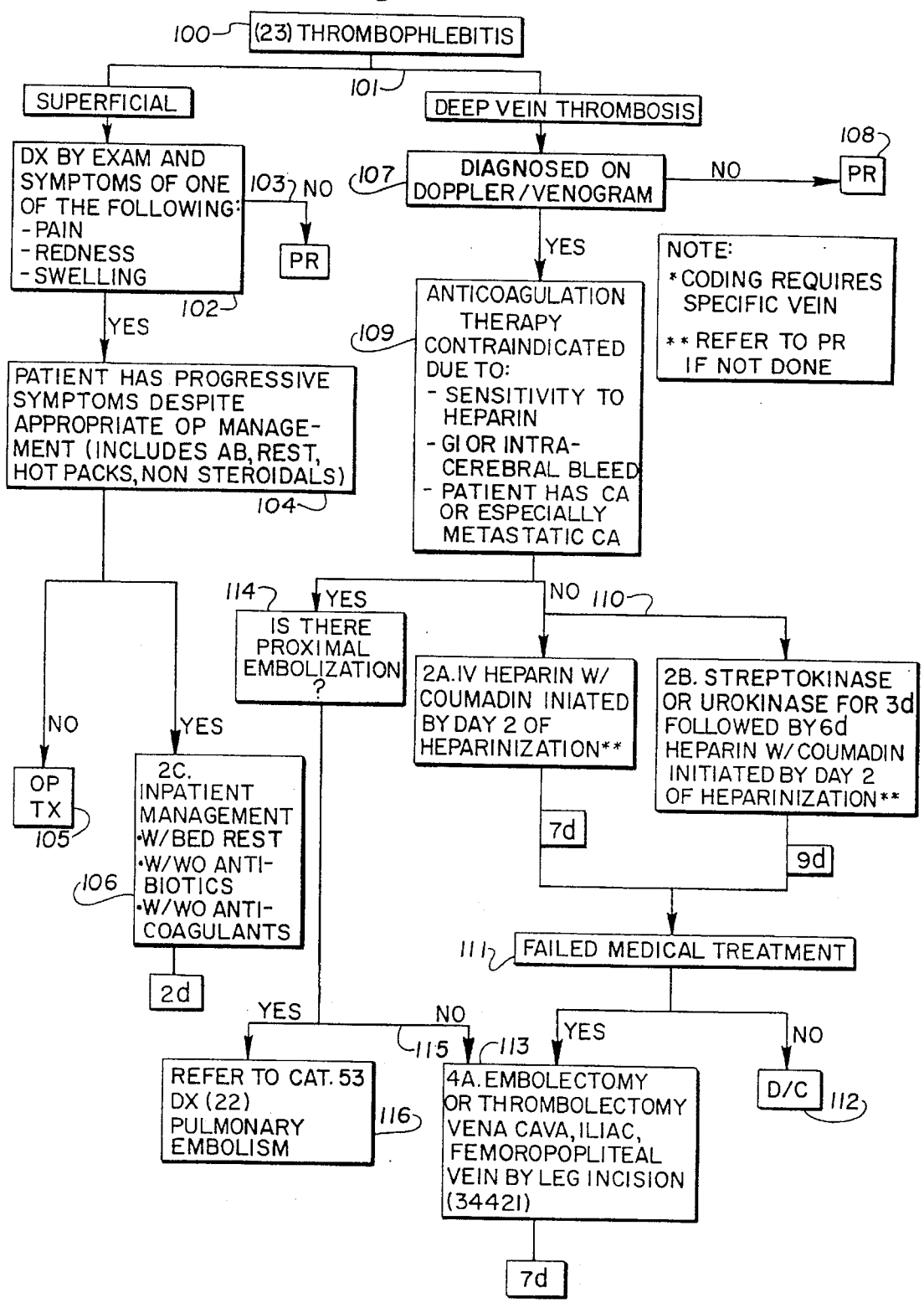
FIG. 18 is a flow chart of the guideline for treatment of thrombophlebitis.

An example of the guideline process for a specific health condition is shown in FIG. 18, a flow chart for the guideline for thrombophlebitis, in conjunction with previously discussed screens shown in FIGS. 11-16, which represent portions of the implementation of the flow chart of FIG. 18. This flow chart does not include all information presented to the user that would appear on the terminal screen. For example, at step 106 the flow chart shows only the guideline treatment code and treatment text. However, the guideline definition for thrombophlebitis includes and the user would actually be presented with a screen similar to FIG. 16 that would include, the numeric procedure code and resource utilization indicators for each treatment option. Also, the flow chart differs from the actual screens in that screen-displayed questions are answered as "pass" or "fail", which correspond to "yes" or "no", respectively, in the flow chart.

Step 100 is the entry point corresponding to selection of the thrombophlebitis guideline based on the guideline title, as shown in FIG. 11, or by use of a diagnosis code, as shown in FIG. 12a, or a treatment text search, as shown in FIG. 12b. At step 101, the user is asked whether the condition is a superficial or deep vein thrombosis. If the user selects "superficial", at step 102 the user is asked whether the diagnosis by examination and symptoms includes one of the following: pain, redness, or swelling. If the user selects "no", at step 103 Physician Review is the option presented. If the user selects "yes", at step 104 the user is asked whether the patient has progressive symptoms despite appropriate out-patient management. If the user selects "no", at step 105 continuing out-patient treatment is the treatment option. If the user selects "yes", at step 106 a guideline treatment option identified by code 2C is presented.

If the user selects "deep vein thrombophlebitis" at step 101, at step 107 the user is asked whether it was diagnosed on doppler/venogram as shown in FIG. 14. If the user selects "no," at step 108, Physician Review is the option presented.

If the user selects "yes," at step 109, the user is asked whether anticoagulation therapy is contraindicated due to several factors. If the user selects "no," at step 110 two guideline treatment options identified by codes 2A and 2B are presented. No preference between the two treatments is identified. At step 111, the user is asked whether the treatment failed. If the user selects "no", at step 112 the guideline indicates that the individual is to be discharged. If the user selects "yes", at step 113 a new guideline treatment option identified by code 4A is presented.

If at step 109 the user selects "yes", at step 114 the user is asked whether there is proximal embolization. If the user selects "no", at step 115 the guideline treatment option identified by code 4A is presented. If the user selects "yes," at step 116 the user is referred to a separate guideline for a specific diagnosis.

The screens implementing this guideline include all of the questions and conditional branching necessary to navigate through the flowchart of FIG. 18 and reach each of the treatment options or other endpoints shown.

For example, the screens presenting questions would appear similar to FIG. 14 with the current question highlighted. When the guideline reaches a treatment option, the user would be presented with a screen similar to FIG. 15, without the Specialist Review sub-screen, showing guideline treatment options with the guideline-selected treatment(s) highlighted. FIG. 15 reflects the endpoint of a question/answer path yielding two guideline treatment options. FIG. 16 shows the same treatments but differs from FIG. 15 in that the user has additionally entered a proposed and final recommendation treatment in a window called up for that purpose.

E. Alternative Embodiments of the Invention

The above embodiment of the invention is a directive mode whereby the guideline process is self-prompting and the user is only required to answer designated questions. In an alternative embodiment invention, the guidelines can be accessed in a non-directive mode whereby the user can access all questions for a given guideline, to view and selectively answer the questions. At any point, the user can shift back to the directive mode and the questions will again be self-prompting with a question appearing based on the questions already answered in the non-directive mode. Accordingly, the non-directive mode is convenient when a user is obtaining information responsive to questions from another source who does not provide the information in the order of appearance of the questions in the directive mode.

F. Reports

An important feature of the present invention is its ability to capture key data during usage for individual patients and cases. This enables the user to track and analyze patterns of care across defined populations in order to understand trends and variations for planning purposes. In addition, reports can show provider profiles, diagnostic decision outcome profiles, as well as procedure decision outcome profiles. On line reports include administrative reports, summary reports and worksheets. Reports may be used by reviewers as work and time management tools and by administrators and managers for summary reports and planning tools. Reports may selected for designated time frames.

Reports sort and summarize case review status in several ways. Case review status includes the following: closed, i.e. closed (C) by normal review procedures or closed by administrative dosed (A); and open, i.e. suspended in questioning (Q), and specialty review (S), or open because the review process has not been completed (O).

There are six types of daily Productivity Reports: operation manager, supervisor, care manager, specialist reviewer, specialist reviewer productivity, and specialist review worksheet. An example of a operation manager report is shown in FIG 19. This is a general summary report which summarizes all open case reviews by medical category 200, i.e., reviews with the status of O, Q or S. A total of all open case reviews for all categories 201 is also listed. Initial reviews 202 as well as extension reviews 203 for each category are listed as well as case reviews in specialty review 204. This report also summarizes case reviews which are still open and over 30 days old 205 and open reviews which are less than or equal to 30 days from the initial review data entry 206.

An example of a supervisor report is shown in FIG. 20. This is a general summary report which summarizes all open case reviews (with status O, Q, or S) and is sorted by care manager (reviewer). A total of all open case reviews for each care manager is listed 207. Initial reviews 208 as well as extension reviews 209 are listed, as well as cases in specialist review 211. This report also summarizes case reviews which are still open and over 30 days old 212 and open case, which are less than or equal to 30 days from the initial review data entry 213.

An example of the care manager report is shown in FIG. 21. This is a general summary report which summarizes all open case reviews (status O, Q or S) by individual care manager (reviewer) 214. This report summarizes for each care manager all open case reviews listing the case ID 215, the most current review date for the review 216, identifying whether the review was initial or extension 217, the specialist review type (physician reviewer, independent medical exam/second opinion appeal) 218, referral reason 219, and the case review guideline name 220. This report is generally used by the care manager for follow-up and tracking and by the specialist reviewer as a time management and daily or weekly work planning tool.

An example of a specialist reviewer report is shown in FIG. 22. This is a general summary report which summarizes open case reviews with specialist status (S) reviewer sorted by reviewer ID, case ID, and review date. This report summarizes for each specialist reviewer 221 all open case reviews listing the case ID 222, the most current review date for the review 223, identifying whether the review was initial or extension 224, the specialist review type (clinical reviewer, physician reviewer, independent medical exam/second opinion, appeal) 225, referral reason 226, and the case review guideline name 227. This report is generally used by the specialist reviewer for follow-up and tracking and as a daily or weekly planning tool.

An example of the specialist reviewer productivity report is shown in FIG. 23 . This summarizes reviews with a specialist review status (S) sorted by medical category and specialist review type, case ID and review date. For each of these the following are listed: the case ID 228 with the most current review date for the review 229, whether the review was initial or extension 230, specialist identification number 231, referral reason 232 and the case review guideline name 233.

An example of a specialist review work sheet is shown in FIGS. 24A and 24B. This report summarizes pertinent information for a case review which needs a specialist review. This would most commonly be used for physician review although it can be used for clinical review, independent medical exam/second opinion or appeal. The report lists the specialist reviewer 234, the case 235 and clinician ID 236, the proposed treatment 237 and guideline treatment 238 with appropriate resources downloaded with the software. Questions passed and failed are summarized 239 and the reason for the specialist review 240 is identified. Note text 241 which has been entered for the case is included. This report is completed by the care manager (reviewer), printed and distributed to the appropriate specialist reviewer. The specialist reviewer would discuss the case with the appropriate person, complete the final recommendation 242 and outcome and return the worksheet to the care manager who would enter the reason code 243, the final recommendation treatment 242 and care changed data 243a into the case review file.

Information management reports identify overall volume and patterns of care including diagnosis, therapeutic selection and resource use. From these reports, you can determine the level of effectiveness or impact related to each guideline use. You can also use the reports for quality measurement and planning by identifying where variations are occurring and how they are resolved at the initial guideline level. Reports may be selected by date in either clinician identification number or reviewer identification number or both. They are sorted automatically by specialty area.

An example of a reporting period summary shown in FIG. 25. This report gives an overall summary of all cases in reviews. It lists case volume 244 (number of total cases), review volume 245 (number of individual reviews), the number of physicians 246, and the number of different guidelines used for initial and extension reviews 247. This report may be sorted for a specific time.

An example of a guideline frequency report is shown in FIG. 26. This report lists in how many cases a particular guideline is used 248. The percent of cases using each guideline 249, and the percent of total cases that guideline represents 250 are also listed.

An example of a patterns of care report is shown in FIG. 27. This report lists the total number of cases using the various guidelines 251. The proposed treatment(s) for each guideline 252 are listed with the number of cases for each 253. Proposed average length of stay 254 and average final recommendation length of stay 255 are also listed for each guideline proposed treatment. This report can also be sorted by overall total or clinician identification number.

An example of a quality management and planning (aggregate) report is shown in FIG. 28. This is an aggregate report which lists the total number of cases with the requested diagnosis 256. For each diagnosis guideline requested 256a, the following are listed: proposed 257 and final treatment combination 258, number of total cases with that combination 259, percent of total cases 260, what percent went to specialist review 261, how many varied from the guideline 262, the type of guideline variance 263, the number of times each variance code was used 264 and the percent of care changed by the treating physician/care provider 265.

An example of a quality management and planning (for each component) report is shown in FIG. 29. This report is sorted by guideline 266, proposed treatment 267, and final recommendation 268. This report is a more detailed report and is a subset of the aggregate quality management and planning report. It lists the three categories of setting 269, preoperative days 270 and length of stay 271. The total number of cases are listed 272. For each guideline in each category, the following are listed: proposed 273 and final recommendation treatment 274, number of cases under each category 275, percent of the cases that carry the proposed/final combination 276, percent to specialist review 277, percent of cases with extensions (stay beyond the initial plan) 278, the number with a guideline variance 279, the type of guideline variance 280, the number of times each variance code was used 280a, and the percent of care changed by the treating physician 281.

An example of the effectiveness report is shown in FIG. 30. This report provides a breakdown by guideline 282 of the results of its use (or impact) on the following areas: percentage of reviews where proposed treatment selection was impacted 283, percentage of reviews where proposed resources were impacted 284, percentage of reviews where both treatment selection and proposed resources were impacted 285, and the percentage of total cases impacted 286 and total cases 287.

Also of significance are reports produced by the system 300 containing the raw data for cases. These data can be analyzed in many ways to provide information useful for the development or improvement of guidelines. As such, these data are of interest to the system developer rather than the system user.

Although the description of the preferred embodiment has been presented, it is contemplated that various changes could be made without deviating from the spirit of the present invention. Accordingly, it is intended that the scope of the present invention be dictated by the appended claims rather than by the description of the preferred embodiment.

What is claimed as new and desired to be protected by Letters Patent is:

1. An electronic system for managing medical treatments and resources required for the treatments, wherein a treatment is recommended to a care giver and the care giver proposes a treatment, comprising:

means for entering a user-proposed treatment and the resources required for the proposed treatment;

resource display means for displaying on a display device for a user one or more medical resources required to implement a recommended treatment and those required for the proposed treatment so that the required resources can be readily compared;

treatment comparison means for comparing the resources required for the proposed treatment with the resources required for a recommended treatment, and notifying a user that specialist review is required for a proposed treatment that requires resources that vary from those required for a recommended treatment;

final recommendation for treatment input means for entering a final recommendation for a treatment identified by a care giver and for accepting from a user information to explain any variance in resources between the final recommendation and the recommended treatment.

2. A system according to claim 1 wherein the resources displayed by the means for displaying are a setting for the recommended treatment, a length of stay for the recommended treatment, and a number of preop days for the recommended treatment.

3. A system according to claim 2 further wherein the means for displaying includes means for displaying the resources for the recommended treatment and final recommendation in side-by-side columns, respectively, and for displaying in a third column aligned with the side-by-side columns the reason codes accepted by a user.

4. A system according to claim 3 further wherein the treatment comparison means includes means for accepting from the user a selection of one of at least two different types of specialist review, and for displaying one or more of at least two different reasons for specialist review.

5. A system according to claim 2 further wherein the resource display means includes means for displaying for a recommended treatment whether an assistant surgeon is required for the treatment.

* * * * *